(12) United States Patent
Puria et al.

(10) Patent No.: US 10,516,949 B2
(45) Date of Patent: Dec. 24, 2019

(54) OPTICAL ELECTRO-MECHANICAL HEARING DEVICES WITH SEPARATE POWER AND SIGNAL COMPONENTS

(71) Applicant: EARLENS CORPORATION, Menlo Park, CA (US)

(72) Inventors: Sunil Puria, Boston, MA (US); Jonathan P. Fay, Dexter, MI (US); Lee Felsenstein, Palo Alto, CA (US); James Stone, Saratoga, CA (US); Mead C. Killion, Elk Grove Village, IL (US); Vincent Pluvinage, Atherton, CA (US)

(73) Assignee: Earlens Corporation, Menlo Park, CA (US)

( * ) Notice: Subject to any disclaimer, the term of this patent is extended or adjusted under 35 U.S.C. 154(b) by 0 days.

(21) Appl. No.: 15/926,876

(22) Filed: Mar. 20, 2018

(65) Prior Publication Data

US 2018/0213335 A1 Jul. 26, 2018

Related U.S. Application Data

(63) Continuation of application No. 15/411,880, filed on Jan. 20, 2017, now Pat. No. 9,961,454, which is a
(Continued)

(51) Int. Cl.
*H04R 23/00* (2006.01)
*H04R 25/00* (2006.01)
*A61N 1/36* (2006.01)

(52) U.S. Cl.
CPC ....... *H04R 23/008* (2013.01); *A61N 1/36036* (2017.08); *H04R 25/554* (2013.01);
(Continued)

(58) Field of Classification Search
CPC ............ A61N 1/36036; H04R 2225/31; H04R 23/008; H04R 25/554; H04R 25/606
See application file for complete search history.

(56) References Cited

U.S. PATENT DOCUMENTS 2,763,334 A 9/1956 Starkey
3,209,082 A 9/1965 McCarrell et al.
(Continued)

FOREIGN PATENT DOCUMENTS

AU 2004301961 A1 2/2005
CA 2242545 C 9/2009
(Continued)

OTHER PUBLICATIONS

Kiessling, et al. Occlusion Effect of Earmolds with Different Venting Systems. J Am Acad Audiol. Apr. 2005;16(4):237-49.
(Continued)

*Primary Examiner* — Christine H Matthews
(74) *Attorney, Agent, or Firm* — Wilson Sonsini Goodrich and Rosati, P.C.

(57) ABSTRACT

A device to transmit an audio signal comprises at least one light source configured to transmit the audio signal with at least one wavelength of light. At least one detector is configured to detect the audio signal and generate at least one electrical signal in response to the at least one wavelength of light. A transducer is supported with and configured to vibrate at least one of an eardrum, an ossicle or a cochlea. Active circuitry is coupled to the transducer to drive the transducer in response to the at least one electrical signal, so as to provide the user with high quality sound.

18 Claims, 13 Drawing Sheets

Related U.S. Application Data continuation of application No. 14/988,304, filed on Jan. 5, 2016, now Pat. No. 9,591,409, which is a continuation of application No. 14/219,076, filed on Mar. 19, 2014, now abandoned, which is a continuation of application No. 12/486,116, filed on Jun. 17, 2009, now Pat. No. 8,715,152.

(60) Provisional application No. 61/139,520, filed on Dec. 19, 2008, provisional application No. 61/073,281, filed on Jun. 17, 2008.

(52) U.S. Cl.
CPC ......... *H04R 25/602* (2013.01); *H04R 25/606* (2013.01); *H04R 2225/31* (2013.01)

(56) References Cited

U.S. PATENT DOCUMENTS

| | | |
|---|---|---|
| 3,229,049 A | 1/1966 | Goldberg |
| 3,440,314 A | 4/1969 | Frisch |
| 3,449,768 A | 6/1969 | Doyle |
| 3,526,949 A | 9/1970 | Genovese |
| 3,549,818 A | 12/1970 | Turner |
| 3,585,416 A | 6/1971 | Mellen |
| 3,594,514 A | 7/1971 | Wingrove |
| 3,710,399 A | 1/1973 | Hurst |
| 3,712,962 A | 1/1973 | Epley |
| 3,764,748 A | 10/1973 | Branch et al. |
| 3,808,179 A | 4/1974 | Gaylord |
| 3,870,832 A | 3/1975 | Fredrickson |
| 3,882,285 A | 5/1975 | Nunley et al. |
| 3,965,430 A | 6/1976 | Brandt |
| 3,985,977 A | 10/1976 | Beaty et al. |
| 4,002,897 A | 1/1977 | Kleinman et al. |
| 4,031,318 A | 6/1977 | Pitre |
| 4,061,972 A | 12/1977 | Burgess |
| 4,075,042 A | 2/1978 | Das |
| 4,098,277 A | 7/1978 | Mendell |
| 4,109,116 A | 8/1978 | Victoreen |
| 4,120,570 A | 10/1978 | Gaylord |
| 4,207,441 A | 6/1980 | Chouard |
| 4,248,899 A | 2/1981 | Lyon et al. |
| 4,252,440 A | 2/1981 | Frosch |
| 4,281,419 A | 8/1981 | Treace |
| 4,303,772 A | 12/1981 | Novicky |
| 4,319,359 A | 3/1982 | Wolf |
| 4,334,315 A | 6/1982 | Ono et al. |
| 4,334,321 A | 6/1982 | Edelman |
| 4,338,929 A | 7/1982 | Lundin et al. |
| 4,339,954 A | 7/1982 | Anson et al. |
| 4,357,497 A | 11/1982 | Hochmair et al. |
| 4,380,689 A | 4/1983 | Giannetti |
| 4,428,377 A | 1/1984 | Zollner et al. |
| 4,524,294 A | 6/1985 | Brody |
| 4,540,761 A | 9/1985 | Kawamura et al. |
| 4,556,122 A | 12/1985 | Goode |
| 4,592,087 A | 5/1986 | Killion |
| 4,606,329 A | 8/1986 | Hough |
| 4,611,598 A | 9/1986 | Hortmann et al. |
| 4,628,907 A | 12/1986 | Epley |
| 4,641,377 A | 2/1987 | Rush et al. |
| 4,652,414 A | 3/1987 | Schlaegel |
| 4,654,554 A | 3/1987 | Kishi |
| 4,689,819 A | 8/1987 | Killion |
| 4,696,287 A | 9/1987 | Hortmann et al. |
| 4,729,366 A | 3/1988 | Schaefer |
| 4,741,339 A | 5/1988 | Harrison et al. |
| 4,742,499 A | 5/1988 | Butler |
| 4,756,312 A | 7/1988 | Epley |
| 4,759,070 A | 7/1988 | Voroba et al. |
| 4,766,607 A | 8/1988 | Feldman |
| 4,774,933 A | 10/1988 | Hough et al. |
| 4,776,322 A | 10/1988 | Hough et al. |
| 4,782,818 A | 11/1988 | Mori |
| 4,800,884 A | 1/1989 | Heide et al. |
| 4,800,982 A | 1/1989 | Carlson |
| 4,817,607 A | 4/1989 | Tatge |
| 4,840,178 A | 6/1989 | Heide et al. |
| 4,845,755 A | 7/1989 | Busch et al. |
| 4,865,035 A | 9/1989 | Mori |
| 4,870,688 A | 9/1989 | Voroba et al. |
| 4,918,745 A | 4/1990 | Hutchison |
| 4,932,405 A | 6/1990 | Peeters et al. |
| 4,936,305 A | 6/1990 | Ashtiani et al. |
| 4,944,301 A | 7/1990 | Widin et al. |
| 4,948,855 A | 8/1990 | Novicky |
| 4,957,478 A | 9/1990 | Maniglia |
| 4,963,963 A | 10/1990 | Dorman |
| 4,982,434 A | 1/1991 | Lenhardt et al. |
| 4,999,819 A | 3/1991 | Newnham et al. |
| 5,003,608 A | 3/1991 | Carlson |
| 5,012,520 A | 4/1991 | Steeger |
| 5,015,224 A | 5/1991 | Maniglia |
| 5,015,225 A | 5/1991 | Hough et al. |
| 5,031,219 A | 7/1991 | Ward et al. |
| 5,061,282 A | 10/1991 | Jacobs |
| 5,066,091 A | 11/1991 | Stoy et al. |
| 5,068,902 A | 11/1991 | Ward |
| 5,094,108 A | 3/1992 | Kim et al. |
| 5,117,461 A | 5/1992 | Moseley |
| 5,142,186 A | 8/1992 | Cross et al. |
| 5,163,957 A | 11/1992 | Sade et al. |
| 5,167,235 A | 12/1992 | Seacord et al. |
| 5,201,007 A | 4/1993 | Ward et al. |
| 5,220,612 A | 6/1993 | Tibbetts et al. |
| 5,259,032 A | 11/1993 | Perkins et al. |
| 5,272,757 A | 12/1993 | Scofield et al. |
| 5,276,910 A | 1/1994 | Buchele |
| 5,277,694 A | 1/1994 | Leysieffer et al. |
| 5,282,858 A | 2/1994 | Bisch et al. |
| 5,298,692 A | 3/1994 | Ikeda et al. |
| 5,338,287 A | 8/1994 | Miller et al. |
| 5,360,388 A | 11/1994 | Spindel et al. |
| 5,378,933 A | 1/1995 | Pfannenmueller et al. |
| 5,402,496 A | 3/1995 | Soli et al. |
| 5,411,467 A | 5/1995 | Hortmann et al. |
| 5,425,104 A | 6/1995 | Shennib |
| 5,440,082 A | 8/1995 | Claes |
| 5,440,237 A | 8/1995 | Brown et al. |
| 5,455,994 A | 10/1995 | Termeer et al. |
| 5,456,654 A | 10/1995 | Ball |
| 5,531,787 A | 7/1996 | Lesinski et al. |
| 5,531,954 A | 7/1996 | Heide et al. |
| 5,535,282 A | 7/1996 | Luca |
| 5,554,096 A | 9/1996 | Ball |
| 5,558,618 A | 9/1996 | Maniglia |
| 5,571,148 A | 11/1996 | Loeb et al. |
| 5,572,594 A | 11/1996 | Devoe et al. |
| 5,606,621 A | 2/1997 | Reiter et al. |
| 5,624,376 A | 4/1997 | Ball et al. |
| 5,654,530 A | 8/1997 | Sauer et al. |
| 5,692,059 A | 11/1997 | Kruger |
| 5,699,809 A | 12/1997 | Combs et al. |
| 5,701,348 A | 12/1997 | Shennib et al. |
| 5,707,338 A | 1/1998 | Adams et al. |
| 5,715,321 A | 2/1998 | Andrea et al. |
| 5,721,783 A | 2/1998 | Anderson |
| 5,722,411 A | 3/1998 | Suzuki et al. |
| 5,729,077 A | 3/1998 | Newnham et al. |
| 5,740,258 A | 4/1998 | Goodwin-Johansson |
| 5,742,692 A | 4/1998 | Garcia et al. |
| 5,749,912 A | 5/1998 | Zhang et al. |
| 5,762,583 A | 6/1998 | Adams et al. |
| 5,772,575 A | 6/1998 | Lesinski et al. |
| 5,774,259 A | 6/1998 | Saitoh et al. |
| 5,782,744 A | 7/1998 | Money |
| 5,788,711 A | 8/1998 | Lehner et al. |
| 5,795,287 A | 8/1998 | Ball et al. |
| 5,797,834 A | 8/1998 | Goode |
| 5,800,336 A | 9/1998 | Ball et al. |
| 5,804,109 A | 9/1998 | Perkins |
| 5,804,907 A | 9/1998 | Park et al. |

(56) References Cited

U.S. PATENT DOCUMENTS

| | | |
|---|---|---|
| 5,814,095 A | 9/1998 | Mueller; Gerd et al. |
| 5,824,022 A | 10/1998 | Zilberman et al. |
| 5,825,122 A | 10/1998 | Givargizov et al. |
| 5,836,863 A | 11/1998 | Bushek et al. |
| 5,842,967 A | 12/1998 | Kroll |
| 5,851,199 A | 12/1998 | Peerless et al. |
| 5,857,958 A | 1/1999 | Ball et al. |
| 5,859,916 A | 1/1999 | Ball et al. |
| 5,868,682 A | 2/1999 | Combs et al. |
| 5,879,283 A | 3/1999 | Adams et al. |
| 5,888,187 A | 3/1999 | Jaeger et al. |
| 5,897,486 A | 4/1999 | Ball et al. |
| 5,899,847 A | 5/1999 | Adams et al. |
| 5,900,274 A | 5/1999 | Chatterjee et al. |
| 5,906,635 A | 5/1999 | Maniglia |
| 5,913,815 A | 6/1999 | Ball et al. |
| 5,922,017 A | 7/1999 | Bredberg et al. |
| 5,922,077 A | 7/1999 | Espy et al. |
| 5,935,170 A | 8/1999 | Haakansson et al. |
| 5,940,519 A | 8/1999 | Kuo |
| 5,949,895 A | 9/1999 | Ball et al. |
| 5,951,601 A | 9/1999 | Lesinski et al. |
| 5,984,859 A | 11/1999 | Lesinski |
| 5,987,146 A | 11/1999 | Pluvinage et al. |
| 6,001,129 A | 12/1999 | Bushek et al. |
| 6,005,955 A | 12/1999 | Kroll et al. |
| 6,011,984 A | 1/2000 | Van Antwerp et al. |
| 6,024,717 A | 2/2000 | Ball et al. |
| 6,038,480 A | 3/2000 | Hrdlicka et al. |
| 6,045,528 A | 4/2000 | Arenberg et al. |
| 6,050,933 A | 4/2000 | Bushek et al. |
| 6,068,589 A | 5/2000 | Neukermans |
| 6,068,590 A | 5/2000 | Brisken |
| 6,072,884 A | 6/2000 | Kates |
| 6,084,975 A | 7/2000 | Perkins |
| 6,093,144 A | 7/2000 | Jaeger et al. |
| 6,135,612 A | 10/2000 | Clore |
| 6,137,889 A | 10/2000 | Shennib et al. |
| 6,139,488 A | 10/2000 | Ball |
| 6,153,966 A | 11/2000 | Neukermans |
| 6,168,948 B1 | 1/2001 | Anderson et al. |
| 6,174,278 B1 | 1/2001 | Jaeger et al. |
| 6,175,637 B1 | 1/2001 | Fujihira et al. |
| 6,181,801 B1 | 1/2001 | Puthuff et al. |
| 6,190,305 B1 | 2/2001 | Ball et al. |
| 6,190,306 B1 | 2/2001 | Kennedy |
| 6,208,445 B1 | 3/2001 | Reime |
| 6,216,040 B1 | 4/2001 | Harrison |
| 6,217,508 B1 | 4/2001 | Ball et al. |
| 6,219,427 B1 | 4/2001 | Kates et al. |
| 6,222,302 B1 | 4/2001 | Imada et al. |
| 6,222,927 B1 | 4/2001 | Feng et al. |
| 6,240,192 B1 | 5/2001 | Brennan et al. |
| 6,241,767 B1 | 6/2001 | Stennert et al. |
| 6,259,951 B1 | 7/2001 | Kuzma et al. |
| 6,261,224 B1 | 7/2001 | Adams et al. |
| 6,264,603 B1 | 7/2001 | Kennedy |
| 6,277,148 B1 | 8/2001 | Dormer |
| 6,312,959 B1 | 11/2001 | Datskos |
| 6,339,648 B1 | 1/2002 | McIntosh et al. |
| 6,342,035 B1 | 1/2002 | Kroll et al. |
| 6,354,990 B1 | 3/2002 | Juneau et al. |
| 6,359,993 B2 | 3/2002 | Brimhall |
| 6,366,863 B1 | 4/2002 | Bye et al. |
| 6,374,143 B1 | 4/2002 | Berrang et al. |
| 6,385,363 B1 | 5/2002 | Rajic et al. |
| 6,387,039 B1 | 5/2002 | Moses |
| 6,390,971 B1 | 5/2002 | Adams et al. |
| 6,393,130 B1 | 5/2002 | Stonikas et al. |
| 6,422,991 B1 | 7/2002 | Jaeger |
| 6,432,248 B1 | 8/2002 | Popp et al. |
| 6,434,246 B1 | 8/2002 | Kates et al. |
| 6,434,247 B1 | 8/2002 | Kates et al. |
| 6,436,028 B1 | 8/2002 | Dormer |
| 6,438,244 B1 | 8/2002 | Juneau et al. |
| 6,445,799 B1 | 9/2002 | Taenzer et al. |
| 6,473,512 B1 | 10/2002 | Juneau et al. |
| 6,475,134 B1 | 11/2002 | Ball et al. |
| 6,491,622 B1 | 12/2002 | Kasic, II et al. |
| 6,491,644 B1 | 12/2002 | Vujanic et al. |
| 6,491,722 B1 | 12/2002 | Kroll et al. |
| 6,493,453 B1 | 12/2002 | Glendon |
| 6,493,454 B1 | 12/2002 | Loi et al. |
| 6,498,858 B2 | 12/2002 | Kates |
| 6,507,758 B1 | 1/2003 | Greenberg et al. |
| 6,519,376 B2 | 2/2003 | Biagi et al. |
| 6,523,985 B2 | 2/2003 | Hamanaka et al. |
| 6,536,530 B2 | 3/2003 | Schultz et al. |
| 6,537,200 B2 | 3/2003 | Leysieffer et al. |
| 6,547,715 B1 | 4/2003 | Mueller et al. |
| 6,549,633 B1 | 4/2003 | Westermann |
| 6,549,635 B1 | 4/2003 | Gebert |
| 6,554,761 B1 | 4/2003 | Puria et al. |
| 6,575,894 B2 | 6/2003 | Leysieffer et al. |
| 6,592,513 B1 | 7/2003 | Kroll et al. |
| 6,603,860 B1 | 8/2003 | Taenzer et al. |
| 6,620,110 B2 | 9/2003 | Schmid |
| 6,626,822 B1 | 9/2003 | Jaeger et al. |
| 6,629,922 B1 | 10/2003 | Puria et al. |
| 6,631,196 B1 | 10/2003 | Taenzer et al. |
| 6,643,378 B2 | 11/2003 | Schumaier |
| 6,663,575 B2 | 12/2003 | Leysieffer |
| 6,668,062 B1 | 12/2003 | Luo et al. |
| 6,676,592 B2 | 1/2004 | Ball et al. |
| 6,681,022 B1 | 1/2004 | Puthuff et al. |
| 6,695,943 B2 | 2/2004 | Juneau et al. |
| 6,697,674 B2 | 2/2004 | Leysieffer |
| 6,724,902 B1 | 4/2004 | Shennib et al. |
| 6,726,618 B2 | 4/2004 | Miller |
| 6,726,718 B1 | 4/2004 | Carlyle et al. |
| 6,727,789 B2 | 4/2004 | Tibbetts et al. |
| 6,728,024 B2 | 4/2004 | Ribak |
| 6,735,318 B2 | 5/2004 | Cho |
| 6,754,358 B1 | 6/2004 | Boesen et al. |
| 6,754,359 B1 | 6/2004 | Svean et al. |
| 6,754,537 B1 | 6/2004 | Harrison et al. |
| 6,785,394 B1 | 8/2004 | Olsen et al. |
| 6,792,114 B1 | 9/2004 | Kates et al. |
| 6,801,629 B2 | 10/2004 | Brimhall et al. |
| 6,829,363 B2 | 12/2004 | Sacha |
| 6,831,986 B2 | 12/2004 | Kates |
| 6,837,857 B2 | 1/2005 | Stirnemann |
| 6,842,647 B1 | 1/2005 | Griffith et al. |
| 6,888,949 B1 | 5/2005 | Vanden Berghe et al. |
| 6,900,926 B2 | 5/2005 | Ribak |
| 6,912,289 B2 | 6/2005 | Vonlanthen et al. |
| 6,920,340 B2 | 7/2005 | Laderman |
| 6,931,231 B1 | 8/2005 | Griffin |
| 6,940,988 B1 | 9/2005 | Shennib et al. |
| 6,940,989 B1 | 9/2005 | Shennib et al. |
| D512,979 S | 12/2005 | Corcoran et al. |
| 6,975,402 B2 | 12/2005 | Bisson et al. |
| 6,978,159 B2 | 12/2005 | Feng et al. |
| 7,020,297 B2 | 3/2006 | Fang et al. |
| 7,024,010 B2 | 4/2006 | Saunders et al. |
| 7,043,037 B2 | 5/2006 | Lichtblau et al. |
| 7,050,675 B2 | 5/2006 | Zhou et al. |
| 7,050,876 B1 | 5/2006 | Fu et al. |
| 7,057,256 B2 | 6/2006 | Mazur et al. |
| 7,058,182 B2 | 6/2006 | Kates |
| 7,058,188 B1 | 6/2006 | Allred |
| 7,072,475 B1 | 7/2006 | Denap et al. |
| 7,076,076 B2 | 7/2006 | Bauman |
| 7,095,981 B1 | 8/2006 | Voroba et al. |
| 7,167,572 B1 | 1/2007 | Harrison et al. |
| 7,174,026 B2 | 2/2007 | Niederdrank et al. |
| 7,179,238 B2 | 2/2007 | Hissong |
| 7,181,034 B2 | 2/2007 | Armstrong |
| 7,203,331 B2 | 4/2007 | Boesen |
| 7,239,069 B2 | 7/2007 | Cho |
| 7,245,732 B2 | 7/2007 | Jorgensen et al. |
| 7,255,457 B2 | 8/2007 | Ducharme et al. |
| 7,266,208 B2 | 9/2007 | Charvin et al. |
| 7,289,639 B2 | 10/2007 | Abel et al. |

(56) References Cited

U.S. PATENT DOCUMENTS

| | | |
|---|---|---|
| 7,313,245 B1 | 12/2007 | Shennib |
| 7,315,211 B1 | 1/2008 | Lee et al. |
| 7,322,930 B2 | 1/2008 | Jaeger et al. |
| 7,349,741 B2 | 3/2008 | Maltan et al. |
| 7,354,792 B2 | 4/2008 | Mazur et al. |
| 7,376,563 B2 | 5/2008 | Leysieffer et al. |
| 7,390,689 B2 | 6/2008 | Mazur et al. |
| 7,394,909 B1 | 7/2008 | Widmer et al. |
| 7,421,087 B2 | 9/2008 | Perkins et al. |
| 7,424,122 B2 | 9/2008 | Ryan |
| 7,444,877 B2 | 11/2008 | Li et al. |
| 7,547,275 B2 | 6/2009 | Cho et al. |
| 7,630,646 B2 | 12/2009 | Anderson et al. |
| 7,645,877 B2 | 1/2010 | Gmeiner et al. |
| 7,668,325 B2 | 2/2010 | Puria et al. |
| 7,747,295 B2 | 6/2010 | Choi |
| 7,809,150 B2 | 10/2010 | Natarajan et al. |
| 7,826,632 B2 | 11/2010 | Von Buol et al. |
| 7,853,033 B2 | 12/2010 | Maltan et al. |
| 7,867,160 B2 | 1/2011 | Pluvinage et al. |
| 7,883,535 B2 | 2/2011 | Cantin et al. |
| 7,983,435 B2 | 7/2011 | Moses |
| 8,090,134 B2 | 1/2012 | Takigawa et al. |
| 8,116,494 B2 | 2/2012 | Rass |
| 8,128,551 B2 | 3/2012 | Jolly |
| 8,157,730 B2 | 4/2012 | Leboeuf et al. |
| 8,197,461 B1 | 6/2012 | Arenberg et al. |
| 8,204,786 B2 | 6/2012 | Leboeuf et al. |
| 8,233,651 B1 | 7/2012 | Haller |
| 8,251,903 B2 | 8/2012 | Leboeuf et al. |
| 8,295,505 B2 | 10/2012 | Weinans et al. |
| 8,295,523 B2 | 10/2012 | Fay et al. |
| 8,320,601 B2 | 11/2012 | Takigawa et al. |
| 8,320,982 B2 | 11/2012 | Leboeuf et al. |
| 8,340,310 B2 | 12/2012 | Ambrose et al. |
| 8,340,335 B1 | 12/2012 | Shennib |
| 8,391,527 B2 | 3/2013 | Feucht et al. |
| 8,396,239 B2 | 3/2013 | Fay et al. |
| 8,401,212 B2 | 3/2013 | Puria et al. |
| 8,401,214 B2 | 3/2013 | Perkins et al. |
| 8,506,473 B2 | 8/2013 | Puria |
| 8,512,242 B2 | 8/2013 | Leboeuf et al. |
| 8,526,651 B2 | 9/2013 | Van Hal et al. |
| 8,526,652 B2 | 9/2013 | Ambrose et al. |
| 8,526,971 B2 | 9/2013 | Giniger et al. |
| 8,545,383 B2 | 10/2013 | Wenzel et al. |
| 8,600,089 B2 | 12/2013 | Wenzel et al. |
| 8,647,270 B2 | 2/2014 | Leboeuf et al. |
| 8,652,040 B2 | 2/2014 | Leboeuf et al. |
| 8,684,922 B2 | 4/2014 | Tran |
| 8,696,054 B2 | 4/2014 | Crum |
| 8,696,541 B2 | 4/2014 | Pluvinage et al. |
| 8,700,111 B2 | 4/2014 | Leboeuf et al. |
| 8,702,607 B2 | 4/2014 | Leboeuf et al. |
| 8,715,152 B2 | 5/2014 | Puria et al. |
| 8,715,153 B2 | 5/2014 | Puria et al. |
| 8,715,154 B2 | 5/2014 | Perkins et al. |
| 8,761,423 B2 | 6/2014 | Wagner et al. |
| 8,787,609 B2 | 7/2014 | Perkins et al. |
| 8,788,002 B2 | 7/2014 | Leboeuf et al. |
| 8,817,998 B2 | 8/2014 | Inoue |
| 8,824,715 B2 | 9/2014 | Fay et al. |
| 8,845,705 B2 | 9/2014 | Perkins et al. |
| 8,855,323 B2 | 10/2014 | Kroman |
| 8,858,419 B2 | 10/2014 | Puria et al. |
| 8,885,860 B2 | 11/2014 | Djalilian et al. |
| 8,886,269 B2 | 11/2014 | Leboeuf et al. |
| 8,888,701 B2 | 11/2014 | Leboeuf et al. |
| 8,923,941 B2 | 12/2014 | Leboeuf et al. |
| 8,929,965 B2 | 1/2015 | Leboeuf et al. |
| 8,929,966 B2 | 1/2015 | Leboeuf et al. |
| 8,934,952 B2 | 1/2015 | Leboeuf et al. |
| 8,942,776 B2 | 1/2015 | Leboeuf et al. |
| 8,961,415 B2 | 2/2015 | Leboeuf et al. |
| 8,986,187 B2 | 3/2015 | Perkins et al. |
| 8,989,830 B2 | 3/2015 | Leboeuf et al. |
| 9,044,180 B2 | 6/2015 | Leboeuf et al. |
| 9,049,528 B2 | 6/2015 | Fay et al. |
| 9,055,379 B2 | 6/2015 | Puria et al. |
| 9,131,312 B2 | 9/2015 | Leboeuf et al. |
| 9,154,891 B2 | 10/2015 | Puria et al. |
| 9,211,069 B2 | 12/2015 | Larsen et al. |
| 9,226,083 B2 | 12/2015 | Puria et al. |
| 9,277,335 B2 | 3/2016 | Perkins et al. |
| 9,289,135 B2 | 3/2016 | Leboeuf et al. |
| 9,289,175 B2 | 3/2016 | Leboeuf et al. |
| 9,301,696 B2 | 4/2016 | Leboeuf et al. |
| 9,314,167 B2 | 4/2016 | Leboeuf et al. |
| 9,392,377 B2 | 7/2016 | Olsen et al. |
| 9,427,191 B2 | 8/2016 | Leboeuf et al. |
| 9,497,556 B2 | 11/2016 | Kaltenbacher et al. |
| 9,521,962 B2 | 12/2016 | Leboeuf |
| 9,524,092 B2 | 12/2016 | Ren et al. |
| 9,538,921 B2 | 1/2017 | Leboeuf et al. |
| 9,544,700 B2 | 1/2017 | Puria et al. |
| 9,591,409 B2 | 3/2017 | Puria et al. |
| 9,749,758 B2 | 8/2017 | Puria et al. |
| 9,750,462 B2 | 9/2017 | Leboeuf et al. |
| 9,788,785 B2 | 10/2017 | Leboeuf |
| 9,788,794 B2 | 10/2017 | Leboeuf et al. |
| 9,794,653 B2 | 10/2017 | Aumer et al. |
| 9,801,552 B2 | 10/2017 | Romesburg et al. |
| 9,808,204 B2 | 11/2017 | Leboeuf et al. |
| 9,930,458 B2 | 3/2018 | Freed et al. |
| 9,949,035 B2 | 4/2018 | Rucker et al. |
| 9,949,039 B2 | 4/2018 | Puria et al. |
| 9,949,045 B2 | 4/2018 | Kure et al. |
| 9,961,454 B2 | 5/2018 | Puria et al. |
| 9,964,672 B2 | 5/2018 | Phair et al. |
| 1,000,388 A1 | 6/2018 | Stephanou et al. |
| 10,206,045 B2 | 2/2019 | Kaltenbacher et al. |
| 2001/0003788 A1 | 6/2001 | Ball et al. |
| 2001/0007050 A1 | 7/2001 | Adelman |
| 2001/0024507 A1 | 9/2001 | Boesen |
| 2001/0027342 A1 | 10/2001 | Dormer |
| 2001/0029313 A1 | 10/2001 | Kennedy |
| 2001/0043708 A1 | 11/2001 | Brimhall |
| 2001/0053871 A1 | 12/2001 | Zilberman et al. |
| 2001/0055405 A1 | 12/2001 | Cho |
| 2002/0012438 A1 | 1/2002 | Leysieffer et al. |
| 2002/0025055 A1 | 2/2002 | Stonikas et al. |
| 2002/0029070 A1 | 3/2002 | Leysieffer et al. |
| 2002/0030871 A1 | 3/2002 | Anderson et al. |
| 2002/0035309 A1 | 3/2002 | Leysieffer |
| 2002/0048374 A1 | 4/2002 | Soli et al. |
| 2002/0085728 A1 | 7/2002 | Shennib et al. |
| 2002/0086715 A1 | 7/2002 | Sahagen |
| 2002/0172350 A1 | 11/2002 | Edwards et al. |
| 2002/0183587 A1 | 12/2002 | Dormer |
| 2003/0021903 A1 | 1/2003 | Shlenker et al. |
| 2003/0055311 A1 | 3/2003 | Neukermans et al. |
| 2003/0064746 A1 | 4/2003 | Rader et al. |
| 2003/0081803 A1 | 5/2003 | Petilli et al. |
| 2003/0097178 A1 | 5/2003 | Roberson et al. |
| 2003/0125602 A1 | 7/2003 | Sokolich et al. |
| 2003/0142841 A1 | 7/2003 | Wiegand |
| 2003/0208099 A1 | 11/2003 | Ball |
| 2003/0208888 A1 | 11/2003 | Fearing et al. |
| 2003/0220536 A1 | 11/2003 | Hissong |
| 2004/0019294 A1 | 1/2004 | Stirnemann |
| 2004/0093040 A1 | 5/2004 | Boylston et al. |
| 2004/0121291 A1 | 6/2004 | Knapp et al. |
| 2004/0158157 A1 | 8/2004 | Jensen et al. |
| 2004/0165742 A1 | 8/2004 | Shennib et al. |
| 2004/0166495 A1 | 8/2004 | Greinwald et al. |
| 2004/0167377 A1 | 8/2004 | Schafer et al. |
| 2004/0184732 A1 | 9/2004 | Zhou et al. |
| 2004/0190734 A1 | 9/2004 | Kates |
| 2004/0202339 A1 | 10/2004 | O'Brien et al. |
| 2004/0202340 A1 | 10/2004 | Armstrong et al. |
| 2004/0208333 A1 | 10/2004 | Cheung et al. |
| 2004/0234089 A1 | 11/2004 | Rembrand et al. |
| 2004/0234092 A1 | 11/2004 | Wada et al. |
| 2004/0236416 A1 | 11/2004 | Falotico |

(56) References Cited

U.S. PATENT DOCUMENTS

| | | |
|---|---|---|
| 2004/0240691 A1 | 12/2004 | Grafenberg |
| 2005/0018859 A1 | 1/2005 | Buchholz |
| 2005/0020873 A1 | 1/2005 | Berrang et al. |
| 2005/0036639 A1 | 2/2005 | Bachler et al. |
| 2005/0038498 A1 | 2/2005 | Dubrow et al. |
| 2005/0088435 A1 | 4/2005 | Geng |
| 2005/0101830 A1 | 5/2005 | Easter et al. |
| 2005/0111683 A1 | 5/2005 | Chabries et al. |
| 2005/0117765 A1 | 6/2005 | Meyer et al. |
| 2005/0163333 A1 | 7/2005 | Abel et al. |
| 2005/0190939 A1 | 9/2005 | Fretz et al. |
| 2005/0196005 A1 | 9/2005 | Shennib et al. |
| 2005/0226446 A1 | 10/2005 | Luo et al. |
| 2005/0267549 A1 | 12/2005 | Della Santina et al. |
| 2005/0271870 A1 | 12/2005 | Jackson |
| 2005/0288739 A1 | 12/2005 | Hassler, Jr. et al. |
| 2006/0015155 A1 | 1/2006 | Charvin et al. |
| 2006/0023908 A1 | 2/2006 | Perkins et al. |
| 2006/0058573 A1 | 3/2006 | Neisz et al. |
| 2006/0062420 A1 | 3/2006 | Araki |
| 2006/0074159 A1 | 4/2006 | Lu et al. |
| 2006/0075175 A1 | 4/2006 | Jensen et al. |
| 2006/0107744 A1 | 5/2006 | Li et al. |
| 2006/0129210 A1 | 6/2006 | Cantin et al. |
| 2006/0161227 A1 | 7/2006 | Walsh et al. |
| 2006/0161255 A1 | 7/2006 | Zarowski et al. |
| 2006/0177079 A1 | 8/2006 | Baekgaard Jensen et al. |
| 2006/0177082 A1 | 8/2006 | Solomito et al. |
| 2006/0183965 A1 | 8/2006 | Kasic et al. |
| 2006/0189841 A1 | 8/2006 | Pluvinage et al. |
| 2006/0231914 A1 | 10/2006 | Carey, III |
| 2006/0233398 A1 | 10/2006 | Husung |
| 2006/0237126 A1 | 10/2006 | Guffrey et al. |
| 2006/0247735 A1 | 11/2006 | Honert et al. |
| 2006/0251278 A1 | 11/2006 | Puria et al. |
| 2006/0256989 A1 | 11/2006 | Olsen et al. |
| 2006/0278245 A1 | 12/2006 | Gan |
| 2007/0030990 A1 | 2/2007 | Fischer |
| 2007/0036377 A1 | 2/2007 | Stirnemann |
| 2007/0076913 A1 | 4/2007 | Schanz |
| 2007/0083078 A1 | 4/2007 | Easter et al. |
| 2007/0100197 A1 | 5/2007 | Perkins et al. |
| 2007/0127748 A1 | 6/2007 | Carlile et al. |
| 2007/0127752 A1 | 6/2007 | Armstrong |
| 2007/0127766 A1 | 6/2007 | Combest |
| 2007/0135870 A1 | 6/2007 | Shanks et al. |
| 2007/0161848 A1 | 7/2007 | Dalton et al. |
| 2007/0191673 A1 | 8/2007 | Ball et al. |
| 2007/0201713 A1 | 8/2007 | Fang et al. |
| 2007/0206825 A1 | 9/2007 | Thomasson |
| 2007/0223755 A1 | 9/2007 | Salvetti et al. |
| 2007/0225776 A1 | 9/2007 | Fritsch et al. |
| 2007/0236704 A1 | 10/2007 | Carr et al. |
| 2007/0250119 A1 | 10/2007 | Tyler et al. |
| 2007/0251082 A1 | 11/2007 | Milojevic et al. |
| 2007/0286429 A1 | 12/2007 | Grafenberg et al. |
| 2008/0021518 A1 | 1/2008 | Hochmair et al. |
| 2008/0051623 A1 | 2/2008 | Schneider et al. |
| 2008/0054509 A1 | 3/2008 | Berman et al. |
| 2008/0063228 A1 | 3/2008 | Mejia et al. |
| 2008/0063231 A1 | 3/2008 | Juneau et al. |
| 2008/0064918 A1 | 3/2008 | Jolly |
| 2008/0077198 A1 | 3/2008 | Webb et al. |
| 2008/0089292 A1 | 4/2008 | Kitazoe et al. |
| 2008/0107292 A1 | 5/2008 | Kornagel |
| 2008/0123866 A1 | 5/2008 | Rule et al. |
| 2008/0130927 A1 | 6/2008 | Theverapperuma et al. |
| 2008/0188707 A1 | 8/2008 | Bernard et al. |
| 2008/0298600 A1 | 12/2008 | Poe et al. |
| 2008/0300703 A1 | 12/2008 | Widmer et al. |
| 2009/0016553 A1 | 1/2009 | Ho et al. |
| 2009/0023976 A1 | 1/2009 | Cho et al. |
| 2009/0043149 A1 | 2/2009 | Abel et al. |
| 2009/0076581 A1 | 3/2009 | Gibson |
| 2009/0092271 A1 | 4/2009 | Fay et al. |
| 2009/0097681 A1 | 4/2009 | Puria et al. |
| 2009/0131742 A1 | 5/2009 | Cho et al. |
| 2009/0141919 A1 | 6/2009 | Spitaels et al. |
| 2009/0149697 A1 | 6/2009 | Steinhardt et al. |
| 2009/0157143 A1 | 6/2009 | Edler et al. |
| 2009/0175474 A1 | 7/2009 | Salvetti et al. |
| 2009/0253951 A1 | 10/2009 | Ball et al. |
| 2009/0262966 A1 | 10/2009 | Vestergaard et al. |
| 2009/0281367 A1 | 11/2009 | Cho et al. |
| 2009/0310805 A1 | 12/2009 | Petroff |
| 2009/0316922 A1 | 12/2009 | Merks et al. |
| 2010/0034409 A1 | 2/2010 | Fay et al. |
| 2010/0036488 A1 | 2/2010 | de Juan, Jr. et al. |
| 2010/0048982 A1 | 2/2010 | Puria et al. |
| 2010/0085176 A1 | 4/2010 | Flick |
| 2010/0103404 A1 | 4/2010 | Remke et al. |
| 2010/0111315 A1 | 5/2010 | Kroman |
| 2010/0114190 A1 | 5/2010 | Bendett et al. |
| 2010/0145135 A1 | 6/2010 | Ball et al. |
| 2010/0152527 A1 | 6/2010 | Puria |
| 2010/0171369 A1 | 7/2010 | Baarman et al. |
| 2010/0172507 A1 | 7/2010 | Merks |
| 2010/0177918 A1 | 7/2010 | Keady et al. |
| 2010/0202645 A1 | 8/2010 | Puria et al. |
| 2010/0222639 A1 | 9/2010 | Purcell et al. |
| 2010/0260364 A1 | 10/2010 | Merks |
| 2010/0272299 A1 | 10/2010 | Van Schuylenbergh et al. |
| 2010/0290653 A1 | 11/2010 | Wiggins et al. |
| 2010/0312040 A1 | 12/2010 | Puria et al. |
| 2011/0069852 A1 | 3/2011 | Arndt et al. |
| 2011/0077453 A1 | 3/2011 | Pluvinage et al. |
| 2011/0112462 A1 | 5/2011 | Parker et al. |
| 2011/0116666 A1 | 5/2011 | Dittberner et al. |
| 2011/0125222 A1 | 5/2011 | Perkins et al. |
| 2011/0130622 A1 | 6/2011 | Ilberg et al. |
| 2011/0142274 A1 | 6/2011 | Perkins et al. |
| 2011/0144414 A1 | 6/2011 | Spearman et al. |
| 2011/0144719 A1 | 6/2011 | Perkins et al. |
| 2011/0152601 A1 | 6/2011 | Puria et al. |
| 2011/0152602 A1 | 6/2011 | Perkins et al. |
| 2011/0152603 A1 | 6/2011 | Perkins et al. |
| 2011/0152976 A1 | 6/2011 | Perkins et al. |
| 2011/0164771 A1 | 7/2011 | Jensen et al. |
| 2011/0182453 A1 | 7/2011 | Van Hal et al. |
| 2011/0221391 A1 | 9/2011 | Won et al. |
| 2011/0249845 A1 | 10/2011 | Kates |
| 2011/0249847 A1 | 10/2011 | Salvetti et al. |
| 2011/0258839 A1 | 10/2011 | Probst |
| 2011/0271965 A1 | 11/2011 | Parkins et al. |
| 2012/0008807 A1 | 1/2012 | Gran |
| 2012/0014546 A1 | 1/2012 | Puria et al. |
| 2012/0038881 A1 | 2/2012 | Amirparviz et al. |
| 2012/0039493 A1 | 2/2012 | Rucker et al. |
| 2012/0114157 A1 | 5/2012 | Arndt et al. |
| 2012/0140967 A1 | 6/2012 | Aubert et al. |
| 2012/0217087 A1 | 8/2012 | Ambrose et al. |
| 2012/0236524 A1 | 9/2012 | Pugh et al. |
| 2013/0004004 A1 | 1/2013 | Zhao et al. |
| 2013/0034258 A1 | 2/2013 | Lin |
| 2013/0083938 A1 | 4/2013 | Bakalos et al. |
| 2013/0089227 A1 | 4/2013 | Kates |
| 2013/0230204 A1 | 9/2013 | Monahan et al. |
| 2013/0287239 A1 | 10/2013 | Fay et al. |
| 2013/0303835 A1 | 11/2013 | Koskowich |
| 2013/0308782 A1 | 11/2013 | Dittberner et al. |
| 2013/0308807 A1 | 11/2013 | Burns |
| 2013/0315428 A1 | 11/2013 | Perkins et al. |
| 2013/0343584 A1 | 12/2013 | Bennett et al. |
| 2013/0343585 A1 | 12/2013 | Bennett et al. |
| 2013/0343587 A1 | 12/2013 | Naylor et al. |
| 2014/0003640 A1 | 1/2014 | Puria et al. |
| 2014/0056453 A1 | 2/2014 | Olsen et al. |
| 2014/0153761 A1 | 6/2014 | Shennib et al. |
| 2014/0169603 A1 | 6/2014 | Sacha et al. |
| 2014/0254856 A1 | 9/2014 | Blick et al. |
| 2014/0275734 A1 | 9/2014 | Perkins et al. |
| 2014/0286514 A1 | 9/2014 | Pluvinage et al. |
| 2014/0288356 A1 | 9/2014 | Van Vlem |
| 2014/0288358 A1 | 9/2014 | Puria et al. |

(56) References Cited

U.S. PATENT DOCUMENTS

| | | |
|---|---|---|
| 2014/0296620 A1 | 10/2014 | Puria et al. |
| 2014/0321657 A1 | 10/2014 | Stirnemann |
| 2014/0379874 A1 | 12/2014 | Starr et al. |
| 2015/0021568 A1 | 1/2015 | Gong et al. |
| 2015/0023540 A1 | 1/2015 | Fay et al. |
| 2015/0031941 A1 | 1/2015 | Perkins et al. |
| 2015/0124985 A1 | 5/2015 | Kim et al. |
| 2015/0201269 A1 | 7/2015 | Dahl et al. |
| 2015/0222978 A1 | 8/2015 | Murozaki et al. |
| 2015/0245131 A1 | 8/2015 | Facteau et al. |
| 2015/0271609 A1 | 9/2015 | Puria et al. |
| 2015/0358743 A1 | 12/2015 | Killion |
| 2016/0008176 A1 | 1/2016 | Goldstein |
| 2016/0029132 A1 | 1/2016 | Freed et al. |
| 2016/0064814 A1 | 3/2016 | Jang et al. |
| 2016/0094043 A1 | 3/2016 | Hao et al. |
| 2016/0150331 A1 | 5/2016 | Wenzel |
| 2016/0277854 A1 | 9/2016 | Puria et al. |
| 2016/0302011 A1 | 10/2016 | Olsen et al. |
| 2016/0309265 A1 | 10/2016 | Pluvinage et al. |
| 2016/0309266 A1 | 10/2016 | Olsen et al. |
| 2017/0040012 A1 | 2/2017 | Goldstein |
| 2017/0095167 A1 | 4/2017 | Facteau et al. |
| 2017/0095202 A1 | 4/2017 | Facteau et al. |
| 2017/0150275 A1 | 5/2017 | Puria et al. |
| 2017/0195801 A1 | 7/2017 | Rucker et al. |
| 2017/0195804 A1 | 7/2017 | Sandhu et al. |
| 2017/0195806 A1 | 7/2017 | Atamaniuk et al. |
| 2017/0195809 A1 | 7/2017 | Teran et al. |
| 2018/0007472 A1 | 1/2018 | Puria et al. |
| 2018/0014128 A1 | 1/2018 | Puria et al. |
| 2018/0020291 A1 | 1/2018 | Puria et al. |
| 2018/0020296 A1 | 1/2018 | Wenzel |
| 2018/0063652 A1 | 3/2018 | Perkins et al. |
| 2018/0077503 A1 | 3/2018 | Shaquer et al. |
| 2018/0077504 A1 | 3/2018 | Shaquer et al. |
| 2018/0167750 A1 | 6/2018 | Freed et al. |
| 2018/0213331 A1 | 7/2018 | Rucker et al. |
| 2018/0262846 A1 | 9/2018 | Perkins et al. |
| 2019/0069097 A1 | 2/2019 | Perkins et al. |

FOREIGN PATENT DOCUMENTS

| | | |
|---|---|---|
| CN | 1176731 A | 3/1998 |
| CN | 101459868 A | 6/2009 |
| DE | 2044870 A1 | 3/1972 |
| DE | 3243850 A1 | 5/1984 |
| DE | 3508830 A1 | 9/1986 |
| EP | 0092822 A2 | 11/1983 |
| EP | 0242038 A2 | 10/1987 |
| EP | 0291325 A2 | 11/1988 |
| EP | 0296092 A2 | 12/1988 |
| EP | 0242038 A3 | 5/1989 |
| EP | 0296092 A3 | 8/1989 |
| EP | 0352954 A2 | 1/1990 |
| EP | 0291325 A3 | 6/1990 |
| EP | 0352954 A3 | 8/1991 |
| EP | 1035753 A1 | 9/2000 |
| EP | 1435757 A1 | 7/2004 |
| EP | 1845919 A1 | 10/2007 |
| EP | 1955407 A1 | 8/2008 |
| EP | 1845919 B1 | 9/2010 |
| EP | 2272520 A1 | 1/2011 |
| EP | 2301262 A1 | 3/2011 |
| EP | 2752030 A1 | 7/2014 |
| EP | 3101519 A1 | 12/2016 |
| EP | 2425502 B1 | 1/2017 |
| EP | 2907294 B1 | 5/2017 |
| EP | 3183814 A1 | 6/2017 |
| EP | 3094067 B1 | 10/2017 |
| FR | 2455820 A1 | 11/1980 |
| GB | 2085694 A | 4/1982 |
| JP | S60154800 A | 8/1985 |
| JP | S621726 B2 | 1/1987 |
| JP | S63252174 A | 10/1988 |
| JP | S6443252 A | 2/1989 |
| JP | H09327098 A | 12/1997 |
| JP | 2000504913 A | 4/2000 |
| JP | 2004187953 A | 7/2004 |
| JP | 2004193908 A | 7/2004 |
| JP | 2005516505 A | 6/2005 |
| JP | 2006060833 A | 3/2006 |
| KR | 100624445 B1 | 9/2006 |
| WO | WO-9209181 A1 | 5/1992 |
| WO | WO-9501678 A1 | 1/1995 |
| WO | WO-9621334 A1 | 7/1996 |
| WO | WO-9736457 A1 | 10/1997 |
| WO | WO-9745074 A1 | 12/1997 |
| WO | WO-9806236 A1 | 2/1998 |
| WO | WO-9903146 A1 | 1/1999 |
| WO | WO-9915111 A1 | 4/1999 |
| WO | WO-0022875 A2 | 4/2000 |
| WO | WO-0022875 A3 | 7/2000 |
| WO | WO-0150815 A1 | 7/2001 |
| WO | WO-0158206 A2 | 8/2001 |
| WO | WO-0176059 A2 | 10/2001 |
| WO | WO-0158206 A3 | 2/2002 |
| WO | WO-0239874 A2 | 5/2002 |
| WO | WO-0239874 A3 | 2/2003 |
| WO | WO-03030772 A2 | 4/2003 |
| WO | WO-03063542 A2 | 7/2003 |
| WO | WO-03063542 A3 | 1/2004 |
| WO | WO-2004010733 A1 | 1/2004 |
| WO | WO-2005015952 A1 | 2/2005 |
| WO | WO-2005107320 A1 | 11/2005 |
| WO | WO-2006014915 A2 | 2/2006 |
| WO | WO-2006037156 A1 | 4/2006 |
| WO | WO-2006039146 A2 | 4/2006 |
| WO | WO-2006042298 A2 | 4/2006 |
| WO | WO-2006071210 A1 | 7/2006 |
| WO | WO-2006075169 A1 | 7/2006 |
| WO | WO-2006075175 A1 | 7/2006 |
| WO | WO-2006118819 A2 | 11/2006 |
| WO | WO-2006042298 A3 | 12/2006 |
| WO | WO-2007023164 A1 | 3/2007 |
| WO | WO-2009046329 A1 | 4/2009 |
| WO | WO-2009047370 A2 | 4/2009 |
| WO | WO-2009049320 A1 | 4/2009 |
| WO | WO-2009056167 A1 | 5/2009 |
| WO | WO-2009062142 A1 | 5/2009 |
| WO | WO-2009047370 A3 | 7/2009 |
| WO | WO-2009125903 A1 | 10/2009 |
| WO | WO-2009145842 A2 | 12/2009 |
| WO | WO-2009146151 A2 | 12/2009 |
| WO | WO-2009155358 A1 | 12/2009 |
| WO | WO-2009155361 A1 | 12/2009 |
| WO | WO-2009155385 A1 | 12/2009 |
| WO | WO-2010033932 A1 | 3/2010 |
| WO | WO-2010033933 A1 | 3/2010 |
| WO | WO-2010077781 A2 | 7/2010 |
| WO | WO-2010147935 A1 | 12/2010 |
| WO | WO-2010148345 A2 | 12/2010 |
| WO | WO-2011005500 A2 | 1/2011 |
| WO | WO-2012088187 A2 | 6/2012 |
| WO | WO-2012149970 A1 | 11/2012 |
| WO | WO-2013016336 A2 | 1/2013 |
| WO | WO-2016011044 A1 | 1/2016 |
| WO | WO-2016045709 A1 | 3/2016 |
| WO | WO-2017045700 A1 | 3/2017 |
| WO | WO-2017059218 A1 | 4/2017 |
| WO | WO-2017059240 A1 | 4/2017 |
| WO | WO-2017116791 A1 | 7/2017 |
| WO | WO-2017116865 A1 | 7/2017 |
| WO | WO-2018048794 A1 | 3/2018 |
| WO | WO-2018081121 A1 | 5/2018 |

OTHER PUBLICATIONS

School of Physics Sydney, Australia. Acoustic Compliance, Inertance and Impedance. 1-6. (2018). http://www.animations.physics.unsw.edu.au/jw/compliance-inertance-impedance.htm.

Wikipedia. Inductive Coupling. 1-2 (Jan. 11, 2018) https://en.wikipedia.org/wiki/inductive_coupling.

(56) References Cited

OTHER PUBLICATIONS

Wikipedia. Pulse-density Coupling. 1-4 (Apr. 6, 2017). https://en.wikipedia.org/wiki/Pulse-density_modulation.
Vinge. Wireless Energy Transfer by Resonant Inductive Coupling. Master of Science Thesis. Chalmers University of Technology. 1-83 (2015).
Wikipedia. Resonant Inductive Coupling. 1-11 (Jan. 12, 2018). https://en.wikipedia.org/wiki/Resonant_inductive_coupling#cite_note-13.
Co-pending U.S. Appl. No. 16/013,839, filed Jun. 20, 2018.
Dundas et al. The Earlens Light-Driven Hearing Aid: Top 10 questions and answers. Hearing Review. 2018;25(2):36-39.
Galbraith et al. A wide-band efficient inductive transdermal power and data link with coupling insensitive gain IEEE Trans Biomed Eng. Apr. 1987;34(4):265-75.
Khaleghi et al. Attenuating the ear canal feedback pressure of a laser-driven hearing aid. J Acoust Soc Am. Mar. 2017;141(3):1683.
Khaleghi et al. Attenuating the feedback pressure of a light-activated hearing device to allows microphone placement at the ear canal entrance. IHCON 2016, International Hearing Aid Research Conference, Tahoe City, CA, Aug. 2016.
Khaleghi et al. Mechano-Electro-Magnetic Finite Element Model of a Balanced Armature Transducer for a Contact Hearing Aid. Proc. MoH 2017, Mechanics of Hearing workshop, Brock University, Jun. 2017.
Khaleghi et al. Multiphysics Finite Element Model of a Balanced Armature Transducer used in a Contact Hearing Device. ARO 2017, 40th ARO MidWinter Meeting, Baltimore, MD, Feb. 2017.
Levy et al. Light-driven contact hearing aid: a removable direct-drive hearing device option for mild to severe sensorineural hearing impairment. Conference on Implantable Auditory Prostheses, Tahoe City, CA, Jul. 2017. 1 page.
McElveen et al. Overcoming High-Frequency Limitations of Air Conduction Hearing Devices Using a Light-Driven Contact Hearing Aid. Poster presentation at The Triological Society, 120th Annual Meeting at COSM, Apr. 28, 2017; San Diego, CA.
Notice of Allowance dated Dec. 21, 2017 for U.S. Appl. No. 15/411,880.
Dictionary.com's (via American Heritage Medical Dictionary) online dictionary definition of 'percutaneous'. Accessed on Jun. 3, 2013. 2 pages.
Merriam-Webster's online dictionary definition of 'percutaneous'. Accessed on Jun. 3, 2013. 3 pages.
Hakansson, et al. Percutaneous vs. transcutaneous transducers for hearing by direct bone conduction (Abstract). Otolaryngol Head Neck Surg. Apr. 1990;102(4):339-44.
Mah. Fundamentals of photovoltaic materials. National Solar Power Research Institute. Dec. 21, 1998, 3-9.
Robles, et al. Mechanics of the mammalian cochlea. Physiol Rev. Jul. 2001;81(3):1305-52.
Web Books Publishing, "The Ear," accessed online Jan. 22, 2013, available online Nov. 2, 2007 at http://www.web-books.com/eLibrary/Medicine/Physiology/Ear/Ear.htm.
Wiki. Sliding Bias Variant 1, Dynamic Hearing (2015).
Asbeck, et al. Scaling Hard Vertical Surfaces with Compliant Microspine Arrays, The International Journal of Robotics Research 2006; 25; 1165-79.
Atasoy [Paper] Opto-acoustic Imaging. For BYM504E Biomedical Imaging Systems class at ITU, downloaded from the Internet www2.itu.edu.td—cilesiz/courses/BYM504- 2005-OA504041413. pdf, 14 pages.
Athanassiou, et al. Laser controlled photomechanical actuation of photochromic polymers Microsystems. Rev. Adv. Mater. Sci. 2003; 5:245-251.
Autumn, et al. Dynamics of geckos running vertically, The Journal of Experimental Biology 209, 260-272, (2006).
Autumn, et al., Evidence for van der Waals adhesion in gecko setae, www.pnas.orgycgiydoiy10.1073ypnas.192252799 (2002).
Ayatollahi, et al. Design and Modeling of Micromachined Condenser MEMS Loudspeaker using Permanent Magnet Neodymium-Iron-Boron (Nd—Fe—B). IEEE International Conference on Semiconductor Electronics, 2006. ICSE '06, Oct. 29, 2006-Dec. 1, 2006; 160-166.
Baer, et al. Effects of Low Pass Filtering on the Intelligibility of Speech in Noise for People With and Without Dead Regions at High Frequencies. J. Acost. Soc. Am 112 (3), pt. 1, (Sep. 2002), pp. 1133-1144.
Best, et al. The influence of high frequencies on speech localization. Abstract 981 (Feb. 24, 2003) from www.aro.org/abstracts/abstracts.html.
Birch, et al. Microengineered systems for the hearing impaired. IEE Colloquium on Medical Applications of Microengineering, Jan. 31, 1996; pp. 2/1-2/5.
Boedts. Tympanic epithelial migration, Clinical Otolaryngology 1978, 3, 249-253.
Burkhard, et al. Anthropometric Manikin for Acoustic Research. J. Acoust. Soc. Am., vol. 58, No. 1, (Jul. 1975), pp. 214-222.
Camacho-Lopez, et al. Fast Liquid Crystal Elastomer Swims Into the Dark, Electronic Liquid Crystal Communications. Nov. 26, 2003; 9 pages total.
Carlile, et al. Frequency bandwidth and multi-talker environments. Audio Engineering Society Convention 120. Audio Engineering Society, May 20-23, 2006. Paris, France. 118: 8 pages.
Carlile, et al. Spatialisation of talkers and the segregation of concurrent speech. Abstract 1264 (Feb. 24, 2004) from www.aro.org/abstracts/abstracts.html.
Cheng, et al. A Silicon Microspeaker for Hearing Instruments. Journal of Micromechanics and Microengineering 2004; 14(7):859-866.
Datskos, et al. Photoinduced and thermal stress in silicon microcantilevers. Applied Physics Letters. Oct. 19, 1998; 73(16):2319-2321.
Decraemer, et al. A method for determining three-dimensional vibration in the ear. Hearing Res., 77:19-37 (1994).
Ear. Downloaded from the Internet. Accessed Jun. 17, 2008. 4 pages. URL:<http://wwwmgs.bionet.nsc.ru/mgs/gnw/trrd/thesaurus/Se/ear.html>.
European search report and opinion dated Feb. 6, 2013 for EP Application No. 09767670.4.
European search report and search opinion dated Mar. 4, 2015 for EP Application No. 09815345.5.
European search report and search opinion dated Dec. 3, 2013 for EP Application No. 09836787.3.
Fay. Cat eardrum mechanics. Ph.D. thesis. Disseration submitted to Department of Aeronautics and Astronautics. Standford University. May 2001; 210 pages total.
Fay, et al. Cat eardrum response mechanics. Mechanics and Computation Division. Department of Mechanical Engineering. Standford University. 2002; 10 pages total.
Fay, et al. Preliminary evaluation of a light-based contact hearing device for the hearing impaired. Otol Neurotol. Jul. 2013;34(5):912-21. doi: 10.1097/MAO.0b013e31827de4b1.
Fay, et al. The discordant eardrum, PNAS, Dec. 26, 2006, vol. 103, No. 52, p. 19743-19748.
Fletcher. Effects of Distortion on the Individual Speech Sounds. Chapter 18, ASA Edition of Speech and Hearing in Communication, Acoust Soc.of Am. (republished in 1995) pp. 415-423.
Freyman, et al. Spatial Release from Informational Masking in Speech Recognition. J. Acost. Soc. Am., vol. 109, No. 5, pt. 1, (May 2001); 2112-2122.
Freyman, et al. The Role of Perceived Spatial Separation in the Unmasking of Speech. J. Acoust. Soc. Am., vol. 106, No. 6, (Dec. 1999); 3578-3588.
Fritsch, et al. EarLens transducer behavior in high-field strength MRI scanners. Otolaryngol Head Neck Surg. Mar. 2009;140(3):426-8. doi: 10.1016/j.otohns.2008.10.016.
Gantz, et al. Broad Spectrum Amplification with a Light Driven Hearing System. Combined Otolaryngology Spring Meetings, 2016 (Chicago).
Gantz, et al. Light Driven Hearing Aid: A Multi-Center Clinical Study. Association for Research in Otolaryngology Annual Meeting, 2016 (San Diego).

(56) References Cited

OTHER PUBLICATIONS

Gantz, et al. Light-Driven Contact Hearing Aid for Broad Spectrum Amplification: Safety and Effectiveness Pivotal Study. Otology & Neurotology Journal, 2016 (in review).
Gantz, et al. Light-Driven Contact Hearing Aid for Broad-Spectrum Amplification: Safety and Effectiveness Pivotal Study. Otology & Neurotology. Copyright 2016. 7 pages.
Ge, et al., Carbon nanotube-based synthetic gecko tapes, p. 10792-10795, PNAS, Jun. 26, 2007, vol. 104, No. 26.
Gennum, GA3280 Preliminary Data Sheet: Voyageur TD Open Platform DSP System for Ultra Low Audio Processing, downloaded from the Internet:<<http://www.sounddesigntechnologies.com/products/pdf/37601DOC.pdf>>, Oct. 2006; 17 pages.
Gobin, et al. Comments on the physical basis of the active materials concept. Proc. SPIE 2003; 4512:84-92.
Gorb, et al. Structural Design and Biomechanics of Friction-Based Releasable Attachment Devices in Insects, Integr. Comp_ Biol., 42:1127-1139 (2002).
Hato, et al. Three-dimensional stapes footplate motion in human temporal bones. Audiol. Neurootol., 8:140-152 (Jan. 30, 2003).
Headphones. Wikipedia Entry. Downloaded from the Internet. Accessed Oct. 27, 2008. 7 pages. URL: http://en.wikipedia.org/wiki/Headphones>.
Hofman, et al. Relearning Sound Localization With New Ears. Nature Neuroscience, vol. 1, No. 5, (Sep. 1998); 417-421.
International Preliminary report on patentability dated Jun. 21, 2011 for PCT/US2009/067703.
International search report and written opinion dated Jul. 21, 2010 for PCT/US2009/067703.
International search report and written opinion dated Nov. 23, 2009 for PCT/US2009/047685.
International search report and written opinion dated Dec. 02, 2009 for PCT/US2009/057719.
Izzo, et al. Laser Stimulation of Auditory Neurons: Effect of Shorter Pulse Duration and Penetration Depth. Biophys J. Apr. 15, 2008;94(8):3159-3166.
Izzo, et al. Laser Stimulation of the Auditory Nerve. Lasers Surg Med. Sep. 2006;38(8):745-753.
Izzo, et al. Selectivity of Neural Stimulation in the Auditory System: A Comparison of Optic and Electric Stimuli. J Biomed Opt. Mar.-Apr. 2007;12(2):021008.
Jian, et al. A 0.6 V, 1.66 mW energy harvester and audio driver for tympanic membrane transducer with wirelessly optical signal and power transfer. InCircuits and Systems (ISCAS), 2014 IEEE International Symposium on Jun. 1, 2014. 874-7. IEEE.
Jin, et al. Speech Localization. J. Audio Eng. Soc. convention paper, presented at the AES 112th Convention, Munich, Germany, May 10-13, 2002, 13 pages total.
Khaleghi, et al. Characterization of Ear-Canal Feedback Pressure due to Umbo-Drive Forces: Finite-Element vs. Circuit Models. ARO Midwinter Meeting 2016, (San Diego).
Killion, et al. The case of the missing dots: AI and SNR loss. The Hearing Journal, 1998. 51(5), 32-47.
Killion. Myths About Hearing Noise and Directional Microphones. The Hearing Review. Feb. 2004; 11(2):14, 16, 18, 19, 72 & 73.
Killion. SNR loss: I can hear what people say but I can't understand them. The Hearing Review, 1997; 4(12):8-14.
Lee, et al. A Novel Opto-Electromagnetic Actuator Coupled to the tympanic Membrane. J Biomech. Dec. 5, 2008;41(16):3515-8. Epub Nov. 7, 2008.
Lee, et al. The optimal magnetic force for a novel actuator coupled to the tympanic membrane: a finite element analysis. Biomedical engineering: applications, basis and communications. 2007; 19(3):171-177.
Levy, et al. Characterization of the available feedback gain margin at two device microphone locations, in the fossa triangularis and Behind the Ear, for the light-based contact hearing device. Acoustical Society of America (ASA) meeting, 2013 (San Francisco).
Levy, et al. Extended High-Frequency Bandwidth Improves Speech Reception in the Presence of Spatially Separated Masking Speech. Ear Hear. Sep.-Oct. 2015;36(5):e214-24. doi: 10.1097/AUD.0000000000000161.
Lezal. Chalcogenide glasses—survey and progress. Journal of Optoelectronics and Advanced Materials. Mar. 2003; 5(1):23-34.
Makino, et al. Epithelial migration in the healing process of tympanic membrane perforations. Eur Arch Otorhinolaryngol. 1990; 247: 352-355.
Makino, et al., Epithelial migration on the tympanic membrane and external canal, Arch Otorhinolaryngol (1986) 243:39-42.
Markoff. Intuition + Money: An Aha Moment. New York Times Oct. 11, 2008, p. BU4, 3 pages total.
Martin, et al. Utility of Monaural Spectral Cues is Enhanced in the Presence of Cues to Sound-Source Lateral Angle. JARO. 2004; 5:80-89.
Michaels, et al., Auditory Epithelial Migration on the Human Tympanic Membrane: II. The Existence of Two Discrete Migratory Pathways and Their Embryologic Correlates, The American Journal of Anatomy 189:189-200 (1990).
Moore, et al. Perceived naturalness of spectrally distorted speech and music. J Acoust Soc Am. Jul. 2003;114(1):408-19.
Moore, et al. Spectro-temporal characteristics of speech at high frequencies, and the potential for restoration of audibility to people with mild-to-moderate hearing loss. Ear Hear. Dec. 2008;29(6):907-22. doi: 10.1097/AUD.0b013e31818246f6.
Moore. Loudness perception and intensity resolution. Cochlear Hearing Loss, Chapter 4, pp. 90-115, Whurr Publishers Ltd., London (1998).
Murphy M, Aksak B, Sitti M. Adhesion and anisotropic friction enhancements of angled heterogeneous micro-fiber arrays with spherical and spatula tips. J Adhesion Sci Technol, vol. 21, No. 12-13, p. 1281-1296, 2007.
Murugasu, et al. Malleus-to-footplate versus malleus-to-stapes-head ossicular reconstruction prostheses: temporal bone pressure gain measurements and clinical audiological data. Otol Neurotol. Jul. 2005; 2694):572-582.
Musicant, et al. Direction-Dependent Spectral Properties of Cat External Ear: New Data and Cross-Species Comparisons. J. Acostic. Soc. Am, May 10-13, 2002, vol. 87, No. 2, (Feb. 1990), pp. 757-781.
National Semiconductor, LM4673 Boomer: Filterless, 2.65W, Mono, Class D Audio Power Amplifier, [Data Sheet] downloaded from the Internet:<<http://www.national.com/ds/LM/LM4673.pdf>>; Nov. 1, 2007; 24 pages.
Nishihara, et al. Effect of changes in mass on middle ear function. Otolaryngol Head Neck Surg. Nov. 1993;109(5):889-910.
Notice of allowance dated Mar. 10, 2015 for U.S. Appl. No. 14/339,746.
Notice of Allowance dated Apr. 26, 2017 for U.S. Appl. No. 14/491,572.
Notice of allowance dated May 29, 2014 for U.S. Appl. No. 13/678,889.
Notice of Allowance dated Jun. 12, 2014 for U.S. Appl. No. 13/069,262.
Notice of allowance dated Aug. 21, 2012 for U.S. Appl. No. 12/486,100.
O'Connor, et al. Middle ear Cavity and Ear Canal Pressure-Driven Stapes Velocity Responses in Human Cadaveric Temporal Bones. J Acoust Soc Am. Sep. 2006;120(3):1517-28.
Office action dated Jan. 20, 2012 for U.S. Appl. No. 12/486,100.
Office action dated May 15, 2013 for U.S. Appl. No. 13/069,262.
Office Action dated Aug. 11, 2016 for U.S. Appl. No. 14/491,572.
Office action dated Aug. 14, 2015 for U.S. Appl. No. 13/069,282.
Office action dated Nov. 6, 2014 for U.S. Appl. No. 13/069,282.
Office action dated Nov. 10, 2014 for U.S. Appl. No. 14/339,746.
Office action dated Dec. 11, 2013 for U.S. Appl. No. 13/678,889.
Office action dated Dec. 31, 2013 for U.S. Appl. No. 13/069,262.
Park, et al. Design and analysis of a microelectromagnetic vibration transducer used as an implantable middle ear hearing aid. J. Micromech. Microeng. vol. 12 (2002), pp. 505-511.

(56) References Cited

OTHER PUBLICATIONS

Perkins, et al. Light-based Contact Hearing Device: Characterization of available Feedback Gain Margin at two device microphone locations. Presented at AAO-HNSF Annual Meeting, 2013 (Vancouver).
Perkins, et al. The EarLens Photonic Transducer: Extended bandwidth. Presented at AAO-HNSF Annual Meeting, 2011 (San Francisco).
Perkins, et al. The EarLens System: New sound transduction methods. Hear Res. Feb. 2, 2010; 10 pages total.
Perkins, R. Earlens tympanic contact transducer: a new method of sound transduction to the human ear. Otolaryngol Head Neck Surg. Jun. 1996;114(6):720-8.
Poosanaas, et al. Influence of sample thickness on the performance of photostrictive ceramics, J. App. Phys. Aug. 1, 1998; 84(3):1508-1512.
Puria et al. A gear in the middle ear. ARO Denver CO, 2007b.
Puria, et al. Cues above 4 kilohertz can improve spatially separated speech recognition. The Journal of the Acoustical Society of America, 2011, 129, 2384.
Puria, et al. Extending bandwidth above 4 kHz improves speech understanding in the presence of masking speech. Association for Research in Otolaryngology Annual Meeting, 2012 (San Diego).
Puria, et al. Extending bandwidth provides the brain what it needs to improve hearing in noise. First international conference on cognitive hearing science for communication, 2011 (Linkoping, Sweden).
Puria, et al. Hearing Restoration: Improved Multi-talker Speech Understanding. 5th International Symposium on Middle Ear Mechanics in Research and Otology (MEMRO), Jun. 2009 (Stanford University).
Puria, et al. Imaging, Physiology and Biomechanics of the middle ear: Towards understating the functional consequences of anatomy. Stanford Mechanics and Computation Symposium, 2005, ed Fong J.
Puria, et al. Malleus-to-footplate ossicular reconstruction prosthesis positioning: cochleovestibular pressure optimization. Otol Nerotol. May 2005; 2693):368-379.
Puria, et al. Measurements and model of the cat middle ear: Evidence of tympanic membrane acoustic delay. J. Acoust. Soc. Am., 104(6):3463-3481 (Dec. 1998).
Puria, et al., Mechano-Acoustical Transformations in A. Basbaum et al., eds., The Senses: A Comprehensive Reference, v3, p. 165-202, Academic Press (2008).
Puria, et al. Middle Ear Morphometry From Cadaveric Temporal Bone MicroCT Imaging. Proceedings of the 4th International Symposium, Zurich, Switzerland, Jul. 27-30, 2006, Middle Ear Mechanics in Research and Otology, pp. 259-268.
Puria, et al. Sound-Pressure Measurements in the Cochlear Vestibule of Human-Cadaver Ears. Journal of the Acoustical Society of America. 1997; 101 (5-1): 2754-2770.
Puria, et al. Temporal-Bone Measurements of the Maximum Equivalent Pressure Output and Maximum Stable Gain of a Light-Driven Hearing System That Mechanically Stimulates the Umbo. Otol Neurotol. Feb. 2016;37(2):160-6. doi: 10.1097/MAO.0000000000000941.
Puria, et al. The EarLens Photonic Hearing Aid. Association for Research in Otolaryngology Annual Meeting, 2012 (San Diego).
Puria, et al. The Effects of bandwidth and microphone location on understanding of masked speech by normal-hearing and hearing-impaired listeners. International Conference for Hearing Aid Research (IHCON) meeting, 2012 (Tahoe City).
Puria, et al. Tympanic-membrane and malleus-incus-complex co-adaptations for high-frequency hearing in mammals. Hear Res. May 2010;263(1-2):183-90. doi: 10.1016/j.heares.2009.10.013. Epub Oct. 28, 2009.
Puria. Measurements of human middle ear forward and reverse acoustics: implications for otoacoustic emissions. J Acoust Soc Am. May 2003;113(5):2773-89.
Puria, S. Middle Ear Hearing Devices. Chapter 10. Part of the series Springer Handbook of Auditory Research pp. 273-308. Date: Feb. 9, 2013.
Qu, et al. Carbon Nanotube Arrays with Strong Shear Binding-On and Easy Normal Lifting-Off, Oct. 10, 2008 vol. 322 Science. 238-242.
Roush. SiOnyx Brings "Black Silicon" into the Light; Material Could Upend Solar, Imaging Industries. Xconomy, Oct. 12, 2008, retrieved from the Internet: www.xconomy.com/boston/2008/10/12/sionyx-brings-black-silicon-into-the-light¬material-could-upend-solar-imaging-industries> 4 pages total.
R.P. Jackson, C. Chlebicki, T.B. Krasieva, R. Zalpuri, W.J. Triffo, S. Puria, "Multiphoton and Transmission Electron Microscopy of Collagen in Ex Vivo Tympanic Membranes," Biomedcal Computation at STandford, Oct. 2008.
Rubinstein. How Cochlear Implants Encode Speech, Curr Opin Otolaryngol Head Neck Surg. Oct. 2004;12(5):444-8; retrieved from the Internet: www.ohsu.edu/nod/documents/week3/Rubenstein.pdf.
Sekaric, et al. Nanomechanical resonant structures as tunable passive modulators. App. Phys. Lett. Nov. 2003; 80(19):3617-3619.
Shaw. Transformation of Sound Pressure Level From the Free Field to the Eardrum in the Horizontal Plane. J. Acoust. Soc. Am., vol. 56, No. 6, (Dec. 1974), 1848-1861.
Shih. Shape and displacement control of beams with various boundary conditions via photostrictive optical actuators. Proc. IMECE. Nov. 2003; 1-10.
Song, et al. The development of a non-surgical direct drive hearing device with a wireless actuator coupled to the tympanic membrane. Applied Acoustics. Dec. 31, 2013;74(12):1511-8.
Sound Design Technologies, —Voyager TDTM Open Platform DSP System for Ultra Low Power Audio Processing—GA3280 Data Sheet. Oct. 2007; retrieved from the Internet:<<http://www.sounddes.com/pdf/37601DOC.pdf>>, 15 page total.
Spolenak, et al. Effects of contact shape on the scaling of biological attachments. Proc. R. Soc. A. 2005; 461:305-319.
Stenfelt, et al. Bone-Conducted Sound: Physiological and Clinical Aspects. Otology & Neurotology, Nov. 2005; 26 (6):1245-1261.
Struck, et al. Comparison of Real-world Bandwidth in Hearing Aids vs Earlens Light-driven Hearing Aid System. The Hearing Review. TechTopic: EarLens. Hearingreview.com. Mar. 14, 2017. pp. 24-28.
Stuchlik, et al. Micro-Nano Actuators Driven by Polarized Light. IEEE Proc. Sci. Meas. Techn. Mar. 2004; 151(2):131-136.
Suski, et al. Optically activated ZnO/Si02/Si cantilever beams. Sensors and Actuators A (Physical), 0 (nr: 24). 2003; 221-225.
Takagi, et al. Mechanochemical Synthesis of Piezoelectric PLZT Powder. KONA. 2003; 51(21):234-241.
Thakoor, et al. Optical microactuation in piezoceramics. Proc. SPIE. Jul. 1998; 3328:376-391.
The Scientist and Engineers Guide to Digital Signal Processing, copyright 01997-1998 by Steven W. Smith, available online at www.DSPguide.com.
Thompson. Tutorial on microphone technologies for directional hearing aids. Hearing Journal. Nov. 2003; 56(11):14-16,18, 20-21.
Tzou, et al. Smart Materials, Precision Sensors/Actuators, Smart Structures, and Structronic Systems. Mechanics of Advanced Materials and Structures. 2004; 11:367-393.
Uchino, et al. Photostricitve actuators. Ferroelectrics. 2001; 258:147-158.
Vickers, et al. Effects of Low-Pass Filtering on the Intelligibility of Speech in Quiet for People With and Without Dead Regions at High Frequencies. J. Acoust. Soc. Am. Aug. 2001; 110(2):1164-1175.
Vinikman-Pinhasi, et al. Piezoelectric and Piezooptic Effects in Porous Silicon. Applied Physics Letters, Mar. 2006; 88(11): 11905-111906.
Wang, et al. Preliminary Assessment of Remote Photoelectric Excitation of an Actuator for a Hearing Implant. Proceeding of the 2005 IEEE, Engineering in Medicine and Biology 27th nnual Conference, Shanghai, China. Sep. 1-4, 2005; 6233-6234.
Wiener, et al. On the Sound Pressure Transformation by the Head and Auditory Meatus of the Cat. Acta Otolaryngol. Mar. 1966; 61(3):255-269.

(56) References Cited

OTHER PUBLICATIONS

Wightman, et al. Monaural Sound Localization Revisited. J Acoust Soc Am. Feb. 1997;101(2):1050-1063.

Yao, et al. Adhesion and sliding response of a biologically inspired fibrillar surface: experimental observations, J. R. Soc. Interface (2008) 5, 723-733 doi:10.1098/rsif.2007.1225 Published online Oct. 30, 2007.

Yao, et al. Maximum strength for intermolecular adhesion of nanospheres at an optimal size. J. R. Soc. Interface doi:10.1098lrsif.2008.0066 Published online 2008.

Yi, et al. Piezoelectric Microspeaker with Compressive Nitride Diaphragm. The Fifteenth IEEE International Conference on Micro Electro Mechanical Systems, 2002; 260-263.

Yu, et al. Photomechanics: Directed bending of a polymer film by light. Nature. Sep. 2003; 425:145.

Edinger, J.R. High-Quality Audio Amplifier With Automatic Bias Control. Audio Engineering; Jun. 1947; pp. 7-9.

OPTICAL ELECTRO-MECHANICAL HEARING DEVICES WITH SEPARATE POWER AND SIGNAL COMPONENTS

CROSS-REFERENCE TO RELATED APPLICATIONS

The present application is a continuation of U.S. application Ser. No. 15/411,880 filed Jan. 20, 2017 and issued as U.S. Pat. No. 9,961,454 on May 1, 2018, which is a continuation of U.S. application Ser. No. 14/988,304 filed Jan. 5, 2016 and issued as U.S. Pat. No. 9,591,409 on Mar. 7, 2017, which is a continuation of U.S. application Ser. No. 14/219,076 filed Mar. 19, 2014, which is a continuation of U.S. application Ser. No. 12/486,116, filed Jun. 17, 2009 and issued as U.S. Pat. No. 8,715,152 on May 6, 2014, which claims the benefit under 35 U.S.C. § 119(e) of U.S. Provisional Application Nos. 61/073,281 filed Jun. 17, 2008 and 61/139,520 filed Dec. 19, 2008; the full disclosures of which are incorporated herein by reference in their entirety.

The subject matter of the present application is related to the following provisional applications: 61/073,271, entitled "OPTICAL ELECTRO-MECHANICAL HEARING DEVICES WITH COMBINED POWER AND SIGNAL ARCHITECTURES", filed on Jun. 17, 2008; 61/139,522 filed Dec. 19, 2008, entitled "OPTICAL ELECTRO-MECHANICAL HEARING DEVICES WITH COMBINED POWER AND SIGNAL ARCHITECTURES"; and 61/177,047 filed May 11, 2009, entitled "OPTICAL ELECTRO-MECHANICAL HEARING DEVICES WITH COMBINED POWER AND SIGNAL ARCHITECTURES"; the full disclosures of which are incorporated herein by reference and suitable for combination in accordance with some embodiments of the present invention.

BACKGROUND OF THE INVENTION

1. Field of the Invention

The present invention is related to hearing systems, devices and methods. Although specific reference is made to hearing aid systems, embodiments of the present invention can be used in many applications where tissue is stimulated with at least one of vibration or an electrical current, for example with wireless communication, the treatment of neurological disorders such as Parkinson's, and cochlear implants.

People like to hear. Hearing devices can be used with communication systems and aids to help the hearing impaired. Hearing impaired subjects need hearing aids to verbally communicate with those around them. Open canal hearing aids have proven to be successful in the marketplace because of increased comfort and an improved cosmetic appearance. Another reason why open canal hearing aids can be popular is reduced occlusion of the ear canal. Occlusion can result in an unnatural, tunnel-like hearing effect which can be caused by large hearing aids which block the ear canal. However, a problem that may occur with open canal hearing aids is feedback. The feedback may result from placement of the microphone in too close proximity with the speaker or the amplified sound being too great. Thus, feedback can limit the degree of sound amplification that a hearing aid can provide. In some instances, feedback may be minimized by using non-acoustic means of stimulating the natural hearing transduction pathway, for example stimulating the tympanic membrane and/or bones of the ossicular chain. A permanent magnet or plurality of magnets may be coupled to the eardrum or the ossicles in the middle ear to stimulate the hearing pathway. These permanent magnets can be magnetically driven to cause motion in the hearing transduction pathway thereby causing neural impulses leading to the sensation of hearing. A permanent magnet may be coupled to the eardrum through the use of a fluid and surface tension, for example as described in U.S. Pat. Nos. 5,259,032 and 6,084,975.

However, work in relation to embodiments of the present invention suggests that magnetically driving the hearing transduction pathway may have limitations. The strength of the magnetic field generated to drive the attached magnet may decrease rapidly with the distance from the field generator coil to the permanent magnet. For magnets implanted to the ossicle, invasive surgery may be needed. Coupling a magnet to the eardrum may avoid the need for invasive surgery. However, there can be a need to align the driver coil with the permanent magnet, and placement of the driver coil near the magnet can cause discomfort for the user, in at least some instances.

An alternative approach is a photo-mechanical system, for example, a hearing device may use light as a medium to transmit sound signals. Such systems are described in U.S. Pat. No. 7,289,639 and U.S. Pat. App. No. U.S. Publication Nos. 2006/0189841. The optical output signal can be delivered to an output transducer coupled to the eardrum or the ossicle. Although optical systems may result in improved comfort for the patient, work in relation to embodiments of the present invention suggests that such systems may result in at least some distortion of the signal such that in some instances the sound perceived by the patient may be less than ideal in at least some instances.

Although pulse width modulation can be used to transmit an audio signal with an optical signal, work in relation to embodiments of the present invention suggests that at least some of the known pulse width modulation schemes may not work well with prior hearing devices in at least some instances. A digital signal output can be represented by a train of digital pulses. The pulses can have a duty cycle (the ratio of time in active to the overall period) that varies with the intended analog amplitude level. The pulses can be integrated to find the intended audio signal, which has an amplitude equal to the duty cycle multiplied by the pulse amplitude. When the amplitude of the intended audio signal decreases, the duty cycle can be decreased so that the amplitude of the integrated audio signal drops proportionally. Conversely, when the amplitude of the intended audio signal increases, the duty cycle can be increased so that the amplitude rises proportionally. Analog audio signals may vary positively or negatively from zero. At least some known pulse width modulation schemes may use a quiescent level, or zero audio level, represented by a 50% duty cycle. Decreases in duty cycle from this quiescent level can correspond to negative audio signal amplitude while increases in duty cycle can correspond to positive audio signal amplitude. Because this quiescent level is maintained, significant amounts of power may be consumed in at least some instances. While this amount of power use may not be a problem for larger signal transduction systems, in at least some instances this power use can pose problems for hearing devices, which are preferably small and may use small batteries that are ideally infrequently replaced.

For the above reasons, it would be desirable to provide hearing systems which at least decrease, or even avoid, at least some of the above mentioned limitations of the current hearing devices. For example, there is a need to provide a comfortable hearing device with less distortion and less feedback than current devices.

2. Description of the Background Art

Patents of interest include: U.S. Pat. Nos. 3,585,416, 3,764,748, 5,142,186, 5,554,096, 5,624,376, 5,795,287, 5,800,336, 5,825,122, 5,857,958, 5,859,916, 5,888,187, 5,897,486, 5,913,815, 5,949,895, 6,093,144, 6,139,488, 6,174,278, 6,190,305, 6,208,445, 6,217,508, 6,222,302, 6,422,991, 6,475,134, 6,519,376, 6,626,822, 6,676,592, 6,728,024, 6,735,318, 6,900,926, 6,920,340, 7,072,475, 7,095,981, 7,239,069, 7,289,639, D512,979, and EP1845919. Patent publications of interest include: PCT Publication Nos. WO 03/063542, WO 2006/075175, U.S. Publication Nos. 2002/0086715, 2003/0142841, 2004/0234092, 2006/0107744, 2006/0233398, 2006/075175, 2008/0021518, and 2008/01079292. Commonly owned U.S. Pat. Nos. 5,259,032, 5,276,910, 5,425,104, 5,804,109, 6,084,975, 6,554,761, 6,629,922, U.S. Publication Nos. 2006/0023908, 2006/0189841, 2006/0251278, and 2007/0100197, the complete disclosures of which herein are incorporated herein by reference and suitable for combination in accordance with some embodiments of the present invention, may also be of interest. Journal publications of potential interest include: Ayatollahi et al., "Design and Modeling of Micromachines Condenser MEMS Loudspeaker using Permanent Magnet Neodymium-Iron-Boron (Nd—Fe—B)", *ISCE*, Kuala Lampur, 2006; Birch et al, "Microengineered Systems for the Hearing Impaired", *IEE*, London, 1996; Cheng et al., "A silicon microspeaker for hearing instruments", *J. Micromech. Microeng.,* 14(2004) 859-866; Yi et al., "Piezoelectric microspeaker with compressive nitride diaphragm", *IEEE,* 2006, and Zhigang Wang et al., "Preliminary Assessment of Remote Photoelectric Excitation of an Actuator for a Hearing Implant", *IEEE* Engineering in Medicine and Biology 27th Annual Conference, Shanghai, China, Sep. 1-4, 2005 Other publications of interest include: Gennum GA3280 Preliminary Data Sheet, "Voyager TD™.Open Platform DSP System for Ultra Low Power Audio Processing" and National Semiconductor LM4673 Data Sheet, "LM4673 Filterless, 2.65W, Mono, Class D audio Power Amplifier"; and Lee et al., "The Optimal Magnetic Force For A Novel Actuator Coupled to the Tympanic Membrane: A Finite Element Analysis," Biomedical Engineering: Applications, Basis and Communications, Vol. 19, No. 3(171-177), 2007.

BRIEF SUMMARY OF THE INVENTION

The present invention is related to hearing systems, devices and methods. Embodiments of the present invention can provide improved audio signal transmission which overcomes at least some of the aforementioned limitations of current systems. The systems, devices, and methods described herein may find application for hearing devices, for example open ear canal hearing aides. A transducer can be supported with and configured to vibrate at least one of an eardrum, an ossicle or a cochlea. Active circuitry powered with an optical signal can be used to drive the transducer in response to the optical signal so as to provide the user with high quality sound. Therefore, the user can have the beneficial comfort of optical coupling and the high quality sound of active circuitry.

In a first aspect, embodiments of the present invention provide a device to transmit an audio signal. At least one light source is configured to transmit the audio signal with at least one wavelength of light. At least one detector is configured to detect the audio signal and generate at least one electrical signal in response to the at least one wavelength of light. A transducer is supported with and configured to vibrate at least one of an eardrum, an ossicle or a cochlea. Active circuitry is coupled to at least one detector and the transducer to drive the transducer in response to the electrical signal.

In many embodiments, a power storage device is coupled to the at least one detector and the active circuitry to power the active circuitry with energy from the at least one detector. The power storage device and the active circuitry can be configured with size and mass for support with at least one of the eardrum, the ossicle or the cochlea. The at least one light source and the at least one detector can be configured to supply power to the power storage device and the active circuitry so as to drive the transducer with energy from the at least one light source. The power storage device may comprise at least one of a capacitor or a miniature rechargeable battery.

In many embodiments, the photodetector comprises at least one of as crystalline silicon, amorphous silicon, micromorphous silicon, black silicon, cadmium telluride, copper indium, gallium selenide, or indium gallium arsenide.

In many embodiments, the transducer comprises at least one of a piezo electric transducer, a flex tensional transducer, a wire coil, a magnet or an acoustic speaker. The active circuitry may comprise at least one of a transistor, an amplifier, a logic gate or a flip flop.

In many embodiments, the audio signal transmitted from the at least one light source to the at least one detector comprises a pulse width modulated signal. The pulse width modulated (hereinafter "PWM") signal may comprise at least one of a delta PWM signal, a differential drive PWM signal, a delta-sigma PWM signal or a differential delta-sigma PWM signal.

Many embodiments further comprise circuitry coupled to an input configured to receive the audio signal. The circuitry is coupled to the at least one light source, and the circuitry is configured to adjust an output of the at least one light source to power the active circuitry in response to the audio signal. The circuitry can be configured measure the audio signal to determine energy of the audio signal and to adjust an amount of energy transmitted with the at least one light source in response to the power of the audio signal. For example, the circuitry can be configured to adjust at least one of a DC bias or an amplitude of pulses of the at least one light source in response to the audio signal to power the active circuitry. Alternatively or in combination, the at least one light source may comprise a first light source configured to transmit the audio signal and a second light source configured to transmit power, and the circuitry is configured to adjust and amount of power transmitted with the second light source in response to the audio signal.

In many embodiments, the circuitry comprises a sound processor configured to measure the audio signal and to adjust the output of the at least one light source to power the active circuitry in response to the audio signal.

In another aspect, embodiments of the present invention provide a system to transmit an audio signal. An input transducer assembly comprises at least one light source configured to emit at least one wavelength of light. An output transducer assembly comprises at least one detector configured to detect the at least one wavelength of light, active circuitry coupled to the at least one detector and a transducer electrically coupled to the active circuitry. The transducer is configured to vibrate at least one of an eardrum, an ossicle, or a cochlea of the user in response to the at least one wavelength of light.

In many embodiments, the output transducer assembly is supported with the at least one of the eardrum, the ossicle or the cochlea. The output transducer assembly may comprise a power storage device supported with the at least one of the eardrum, the ossicle. The power storage device can be configured with at least one of a size or a mass to vibrate with the at least one of the eardrum, the ossicle or the cochlea. The active circuitry can be coupled to the detector and the transducer to drive the transducer in response to the at least one wavelength of light. The active circuitry can be configured with at least one of a size or a mass to vibrate with the at least one of the eardrum, the ossicle or the cochlea.

In many embodiments, the input transducer is configured to transmit the at least one wavelength of light as a pulse width modulated signal and wherein the output transducer assembly is configured to vibrate the at least one of the eardrum, the ossicle or the cochlea in response to the pulse width modulated signal.

In many embodiments, the at least one wavelength of light comprises a first wavelength of light and a second wavelength of light, and the at least one light source comprises a first light source configured to emit the first wavelength and a second light source configured to emit the second wavelength of light. The at least one detector comprises a first detector configured to move the transducer with a first movement in response to a first at least one wavelength of light. A second detector is configured to move the transducer with a second movement in response to the second at least one wavelength, in which the second movement is opposite the first movement.

The at least one wavelength of light comprises at least one of an ultraviolet light, a visible light or an infrared light.

In another aspect, embodiments of the present invention provide a method of transmitting an audio signal. At least one wavelength of light is emitted from at least one light source. The at least one wavelength of light is detected to generate and electrical signal. At least one of an eardrum, an ossicle, or a cochlea of a user is vibrated in response to the electrical signal.

In many embodiments, the output transducer assembly is supported with the at least one of the eardrum, the ossicle or the cochlea. The output transducer assembly may comprise a power storage device supported with the at least one of the eardrum, the ossicle or the cochlea. The power storage device may vibrate when the at least one of the eardrum, the ossicle or the cochlea is vibrated. The output transducer assembly may comprise active circuitry supported with the at least one of the eardrum, the ossicle or the cochlea. The active circuitry can be coupled to the detector and the transducer to drive the transducer in response to the at least one wavelength of light. The active circuitry may vibrate when the at least one of the eardrum, the ossicle or the cochlea vibrates.

In another aspect, embodiments of the present invention provide device to stimulate a target tissue. The device comprises at least one light source configured to transmit a pulse width modulated light signal with at least one wavelength of light. At least one detector is coupled to the target tissue to stimulate the target tissue in response to the modulated light signal.

In many embodiments, an implantable detector is configured to stimulate the tissue with at least one of a vibration or a current and wherein the detector is coupled to at least one of a transducer or at least two electrodes. For example, the detector can be configured to stimulate the tissue with the current, and the detector can be coupled to the at least two electrodes. The target tissue may comprise a cochlea of the user, and the modulated light signal may comprise an audio signal.

In another aspect, embodiments of the present invention provide a method of stimulating a target tissue. A pulse width modulated light signal comprising at least one wavelength of light is emitted from at least one light source. The target tissue is stimulated in response to the modulated light signal.

In many embodiments, the target tissue is stimulated with at least one of a vibration or a current. The target tissue can be stimulated with the current, and the implantable detector can be coupled to at least two electrodes and stimulate the tissue in response to the modulated signal comprising the at least one wavelength of light. The target tissue may comprise a cochlea of the user and the modulated light signal may comprise an audio signal.

In another aspect, embodiments of the present invention provide device to transmit an audio signal comprising sound to a user. The device comprises means for transmitting the audio signal and means for detecting the audio signal such that the user hears the sound

DETAILED DESCRIPTION OF THE INVENTION

Embodiments of the present invention can be used in many applications where tissue is stimulated with at least one of vibration or an electrical current, for example with wireless communication, the treatment of neurological disorders such as Parkinson's, and cochlear implants. An optical signal can be transmitted to a photodetector coupled to tissue so as to stimulate tissue. The tissue can be stimulated with at least one of a vibration or an electrical current. For example, tissue can be vibrated such that the user perceives sound. Alternatively or in combination, the tissue such as neural tissue can be stimulated with an electrical current such that the user perceives sound. The optical signal transmission architecture described herein can have many uses outside the field of hearing and hearing loss and can be used to treat, for example, neurological disorders such as Parkinson's.

Embodiments of the present invention can provide optically coupled hearing devices with improved audio signal transmission. The systems, devices, and methods described herein may find application for hearing devices, for example open ear canal hearing aides. Although specific reference is made to hearing aid systems, embodiments of the present invention can be used in any application where sound is amplified for a user, for example with wireless communication and for example with surgical implants to the middle ear and cochlear implants.

As used herein active circuitry encompasses circuitry that can amplify an input signal so as to produce an output signal having more power than the input signal. The active circuitry may comprise at least one of a transistor, an amplifier, a logic gate or a flip flop. The additional power of the output signal can be obtained from a power storage device. The power storage device may comprise at least one of a miniature rechargeable battery or a capacitor. In many embodiments, the power storage device is charged and/or recharged with optical power from a light source, such as the light source used to transmit the audio signal. At least one of the active circuitry or the power storage device can be configured to vibrate with the transducer.

Figure 1:
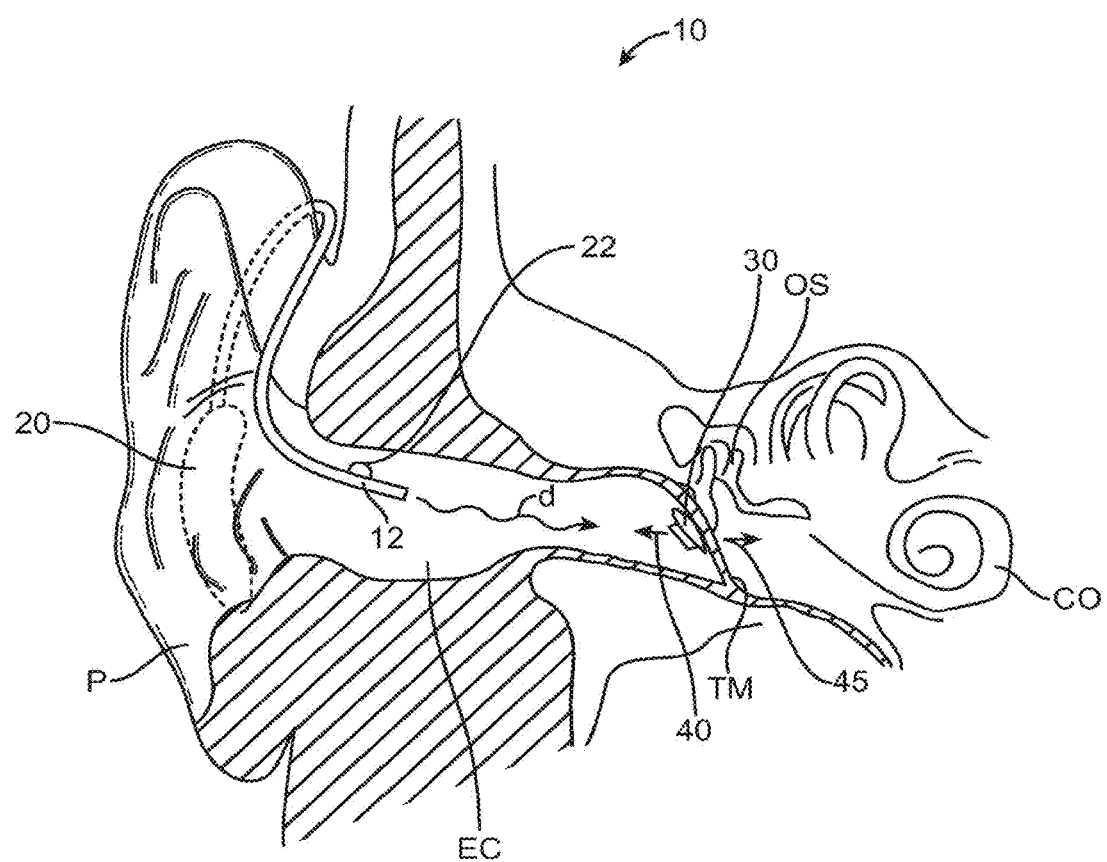
FIG. 1 shows a hearing system using photo-electro-mechanical sound transduction, according to embodiments of the present invention.

A hearing aid system using photo-electro-mechanical transduction is shown in FIG. 1. The hearing system 10 includes an input transducer assembly 20 and an output transducer assembly 30. As shown in FIG. 1, the input transducer assembly 20 is located at least partially behind the pinna P, although the input transducer assembly may be located at many sites such as in pinna P or entirely within ear canal EC, for example, as with microphone 22. The input transducer assembly 20 receives a sound input, for example an audio sound. With hearing aids for hearing impaired individuals, the input is ambient sound. In this case, input transducer assembly can include a suitable amplifier or other electronic interface. In some embodiments, the input may be an electronic sound signal from a sound producing or receiving device, such as a telephone, a cellular telephone, a Bluetooth connection, a radio, a digital audio unit, and the like.

Input transducer assembly 20 includes a light source, such as an LED or a laser diode. The light source produces a modulated light output based on the sound input. The light output comprises at least one wavelength λ of light that is delivered to a target location near or adjacent to output transducer assembly 30 by a light transmission element 12 which traverses ear canal EC. Light transmission element 12 may be an optic fiber or bundle of optic fibers. The light output comprising at least one wavelength λ is selected to couple to the output transducer assembly 30 to provide a signal to output transducer assembly 30 so that it can produce mechanical vibrations. For example, light output comprising at least one wavelength λ may cause output transducer assembly 30 to move in a first direction 40 or in a second direction 45. Second direction 45 may be opposite first direction 40. The at least one wavelength λ may comprise a plurality of wavelengths, for example a first wavelength to move the transducer of the transducer assembly in first direction 40 and a second wavelength to move the transducer of the transducer assembly in second direction 45. When properly coupled to the subject's hearing transduction pathway, the mechanical vibrations induces neural impulses in the subject which are interpreted by the subject as the original sound input, or at least something reasonably representative of the original sound input.

The output transducer assembly 30 can be configured to couple to some point in the hearing transduction pathway of the subject in order to induce neural impulses which are interpreted as sound by the subject. Preferably, the output transducer assembly 30 can couple to the tympanic membrane TM. Alternatively, the output transducer assembly 15 may couple to a bone in the ossicular chain OS or directly to the cochlea CO where it is positioned to vibrate fluid within the cochlea CO. Specific points of attachment, for example to at least one the tympanic membrane, an ossicle of the middle ear or the cochlea, are described in prior U.S. Pat. Nos. 5,259,032; 5,456,654; 6,084,975; and 6,629,922 and 7,289,639.

The input transducer assembly 20 can be configured in many ways to couple to the output transducer assembly 30. For example, the input transducer assembly 20 may comprise a behind the ear unit (hereinafter "BTE"), such that many of the electronic components can be positioned behind the ear with light transmission element 12 extending into the ear canal. Alternatively, the input transducer assembly 20 may comprise a module configured for placement in the ear canal, for example as described in U.S. Pat. No. 7,289,639. The circuitry of the input transducer assembly as described herein can be sized and configured for placement in the ear canal, such that the user hears high quality sound with an input transducer assembly configured for placement in the ear canal.

Figure 2:
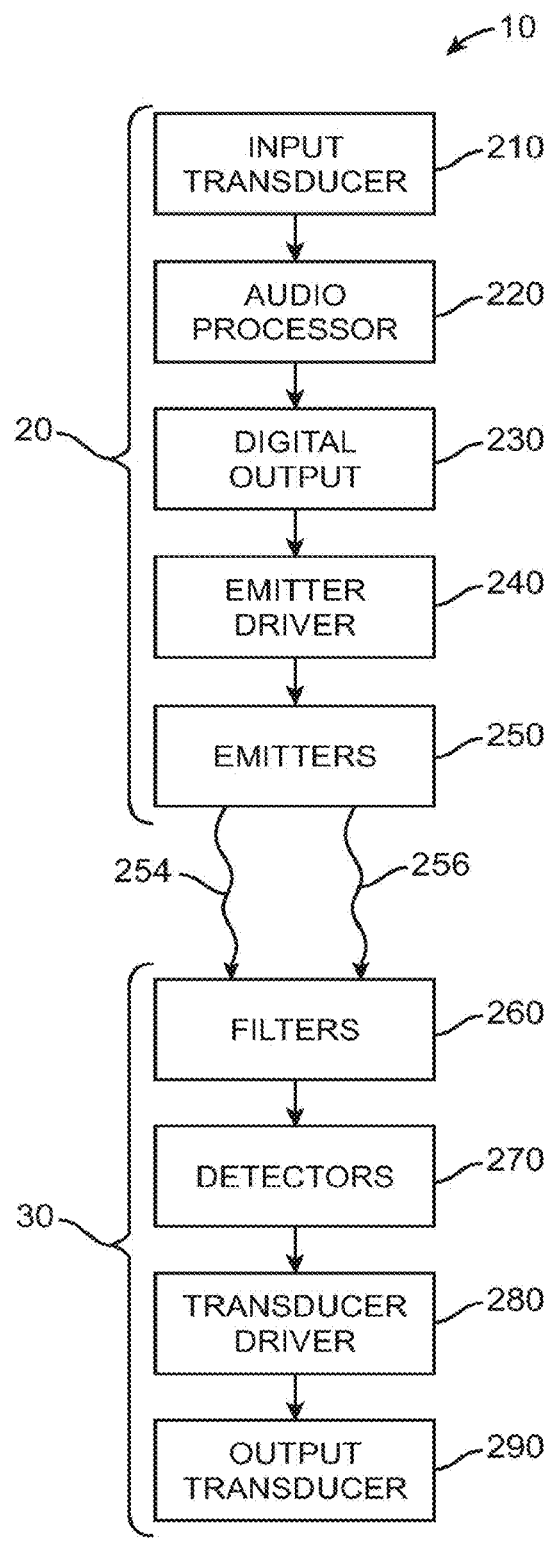
FIG. 2 is a graphical representation of components of the hearing system as in FIG. 1.

FIG. 2 graphically depicts components of hearing system 10. The input transducer assembly 20 may comprise an input transducer 210, an audio processor 220, an emitter driver 240 and emitters 250. The output transducer assembly 30 may comprise filters 260, detectors 270, a transducer driver 280 and an output transducer 290. Input transducer 210 takes ambient sound and converts it into an analog electrical signal. Input transducer 210 often includes a microphone which may be placed in the ear canal, behind the ear, in the pinna, or generally in proximity with the ear. Audio processor 220 may provide a frequency dependent gain to the analog electrical signal. The analog electrical signal is converted to a digital electrical signal by digital output 230. Audio processor 220 may comprise many audio processors, for example an audio processor commercially available from Gennum of Corporation of Burlington, Canada and GA3280 hybrid audio processor commercially available from Sound Design Technologies, Ltd. of Burlington Ontario, Canada. Digital output 230 includes a modulator, for example, a pulse-width modulator or a delta-sigma converter. Emitter driver 240 processes the digital electrical signal so that it is specific to optical transmission and the power requirements of emitters 250.

Emitters 250 produce a light output representative of the electrical signal. For a dual component electrical signal, emitters 250 can include two light sources, one for each component, and produce two light output signals 254, 256. The light source may be, for example, an LED or a laser diode, and the light output may be in the infrared, visible, or ultraviolet wavelength. For example, the light source may comprise an LED that emits at least one wavelength of light comprising a central wavelength and a plurality of wavelengths distributed about the central wavelength with a bandwidth of about 40 nm. The light source may comprise a laser diode that emits at least one wavelength of light comprising a central wavelength with a bandwidth no more than about 2 nm, for example no more than 1 nm. The first at least one wavelength from the first source can be different from the second at least one wavelength from the second source, for example different by at least 80 nm, such that the first at least one wavelength can be separated from the second at least one wavelength of light. The first at least one wavelength may comprise a first bandwidth, for example 60 nm, and the second at least one wavelength may comprise a second bandwidth, for example 60 nm, and the first at least one wavelength can be different from the second at least one wavelength by at least the first bandwidth and the second bandwidth, for example 120 nm.

The light output signals travel along a single or multiple optical paths though the ear canal, for example, via an optic fiber or fibers. The light output signals may spatially overlap. The signals are received by an output transducer assembly which can be placed on the ear canal.

The output transducer assembly comprises components to respond to the optical signal so as to vibrate at least one of the eardrum, the ossicles or the cochlea in response to the optical signal. Detectors 270 receive the light output signals. Detectors 270 include at least one photodetector provided for each light output signal. A photodetector may be, for example, a photodiode, a photovoltaic, or the like. Filters 260 are optionally provided along the optical path. Filters 260 separate the light output signals. For example, a first filter may be provided to transmit the wavelength of output 254 while a second filter transmits the wavelength of output 256. Filters may be any one of the thin film, interference, dichroic, or gel types with either band-pass, low-pass, or high-pass characteristics. For example, the band-pass characteristics may be configured to pass the at least one wavelength of the source, for example configured with a 30 nm bandwidth to pass a 10 nm bandwidth source, as described above. The low-pass and high-pass maybe combined to pass only one preferred wavelength using the low-pass filter and the other wavelength using the high-pass filter.

Each of detectors 270 may comprise at least one photovoltaic material such as crystalline silicon, amorphous silicon, micromorphous silicon, black silicon, cadmium telluride, copper indium gallium selenide, and the like. In some embodiments at least one of photodetectors 270 comprises black silicon, for example as described in U.S. Pat. Nos. 7,354,792 and 7,390,689 and available under from SiOnyx, Inc. of Beverly, Mass. The black silicon may comprise shallow junction photonics manufactured with semiconductor process that exploits atomic level alterations that occur in materials irradiated by high intensity lasers, such as a femto-second laser that exposes the target semiconductor to high intensity pulses as short as one billionth of a millionth of a second. Crystalline materials subject to these intense localized energy events may under go a transformative change, such that the atomic structure becomes instantaneously disordered and new compounds are "locked in" as the substrate re-crystallizes. When applied to silicon, the result can be a highly doped, optically opaque, shallow junction interface that is many times more sensitive to light than conventional semiconductor materials.

Transducer driver 280 converts the light output signals back into digital electrical signals which carries audio information. Output transducer 290 converts the electrical signal representative of sound into a mechanical energy which then is transmitted to a patient's hearing transduction pathway, causing the sensation of hearing. The transducer may be a piezoelectric transducer, a flex tensional transducer, a magnet and wire coil, or a microspeaker.

Alternatively to the transducer driver 280, at least two electrodes can be coupled to the at least one of the detectors, such that the user perceives sound in response to tissue stimulation from the at least two electrodes. The at least two electrodes can be configured for placement at least partially in the cochlea of the user, such that the user perceives sound in response to the light output.

Many of he above components can be sized and positioned so as to fit within the BTE unit positioned behind the ear.

Figure 2A:
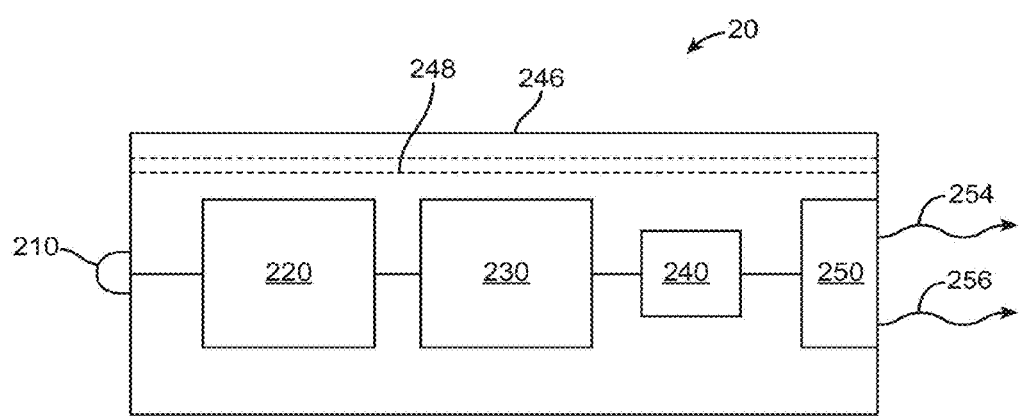
FIG. 2A shows an ear canal module comprising the components of FIG. 2, according to embodiments of the present invention.

FIG. 2A shows components of input transducer assembly 20 positioned in a module sized to fit in the ear canal of the user. The module may comprise an outer housing 246 shaped to the ear of the user, for example with a mold of the ear canal. The module may comprise a channel extending from a proximal end where the input transducer 210 is located to a distal end from which light is emitted, such that occlusion is decreased.

Figure 3:
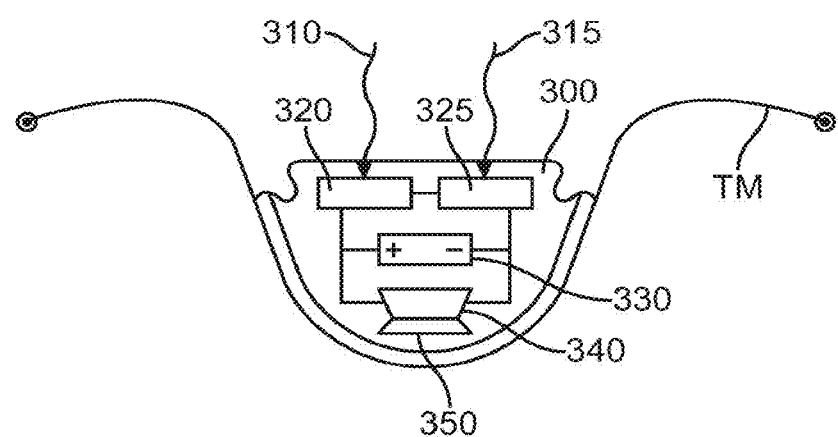
FIG. 3 shows a photo-electro-mechanical transducer assembly for use with the system as in FIGS. 1 and 2.

FIG. 3 shows an output transducer assembly 300 placed on the tympanic membrane TM, also referred to as the eardrum. Output transducer assembly 300 comprises circuitry which is used to convert light output signals into electrical energy and mechanical energy. Output transducer assembly 300 includes photodetectors 320, 325. Photodetectors 320, 325 detect light output signals 310, 315, respectively, and convert the light output into electrical signals. Output transducer assembly 300 comprises a power storage component 330. Power storage component 330 may comprise at least one of a capacitor, a miniature rechargeable battery, or known power storage device. The power storage component can provide electrical power for an active circuitry component 340. The active circuitry component may comprise at least one of an amplifier or a flip flop. The active circuitry component 340 is coupled to photodetectors 320, 325 to receive the light output signals 320, 325, respectively. Optical filters, as described above, can be used. The active circuitry component applies electrical energy to the load in response to input signals 320, 325 respectively. The electrical signals reach load 350 which converts the electrical signals into a mechanical output such as a vibration. Load 350 may comprise a load from many known transducers, for example at least one of a piezoelectric transducer, a flex tensional transducer, or a wire coil coupled to an external magnet.

In some embodiments, the output transducer assembly and output circuitry can be positioned on and/or supported with an ossicle, for example as described in U.S. Pat. No. 7,289,639.

Figure 3A:
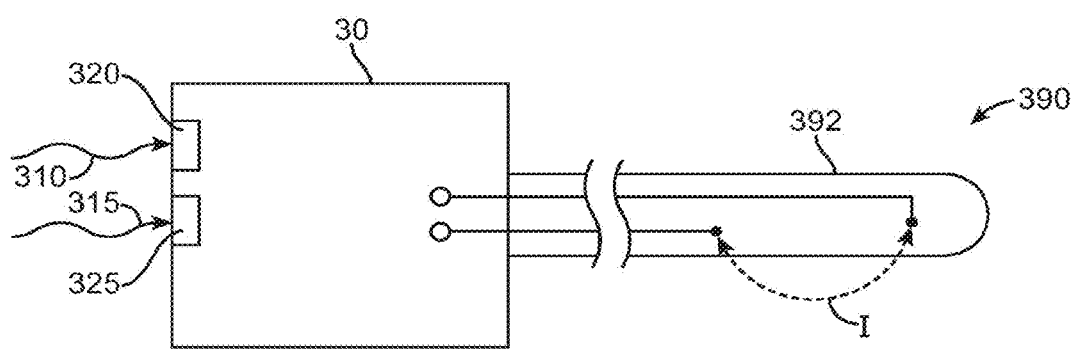
FIG. 3A shows an implantable output assembly for use with components of a system as in FIGS. 1 and 2.

FIG. 3A shows an implantable output assembly for use with components of a system as in FIGS. 1 and 2. The implantable output assembly 30 may comprise at least two electrodes 390 and an extension 392 configured to extend to a target tissue, for example the cochlea. The implantable output assembly can be configured for placement in many locations and to stimulate many target tissues, such as neural tissue. The at least two electrodes can be coupled to the circuitry so as to comprise a load in a manner similar to transducer 310 described above. A current I flows between the electrodes in response to the optical signal. For example the implantable output assembly can be configured to extend from the middle ear to the cochlea. The implantable output assembly can be configured in many ways to stimulate a target tissue, for example to treat Parkinson's.

Figure 4A:
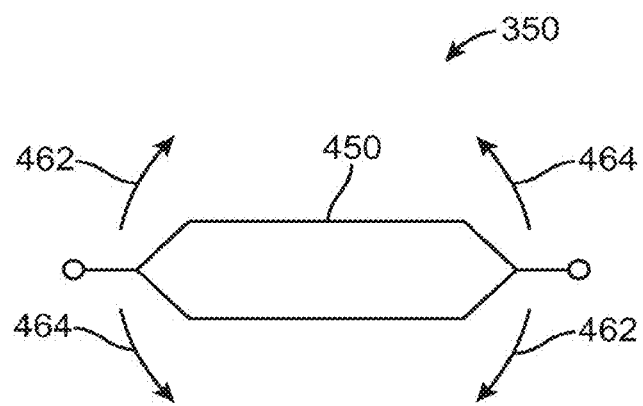
FIG. 4A shows a first rotational movement comprising first rotation with a flex tensional transducer and a second rotation movement comprising a second rotation opposite the first rotation, according to embodiments of the present invention.

Load 350 may comprise a flex tensional transducer 450. FIG. 4A shows a first rotational movement comprising first rotation 462 with a flex tensional transducer 450 and a second rotation movement comprising a second rotation 464 opposite the first rotation.

Figure 4B:
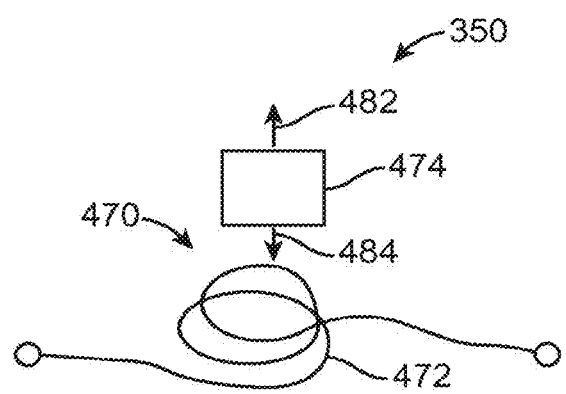
FIG. 4B shows a translational movement in a first direction with a coil and magnet and a second translational movement in a second direction opposite the first direction; according to embodiments of the present invention.

In some embodiments, load 350 may comprise a transducer 470 comprising a coil 472 magnetically coupled to a magnet 474. FIG. 4B shows a first translational movement in a first direction 482 and a second translational movement in a second direction 484 opposite the first direction with transducer 470 comprising a coil 472 and magnet 474.

Figure 5:
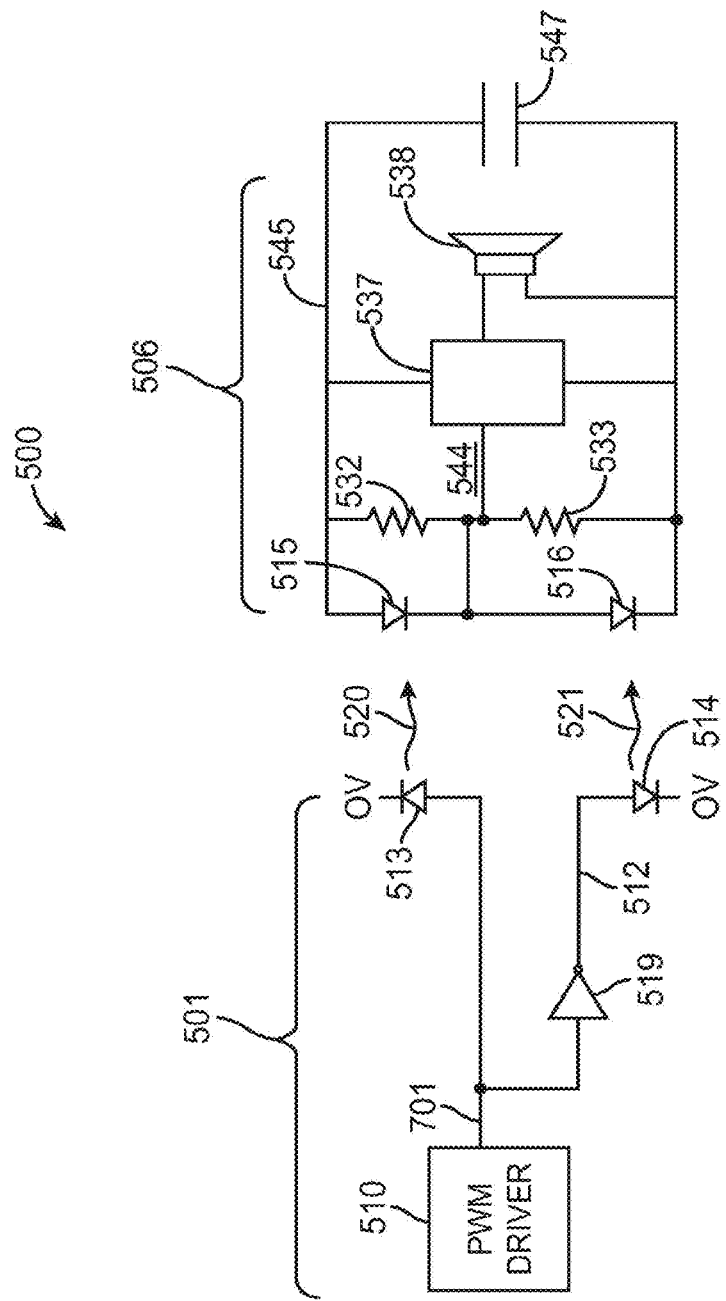
FIG. 5 shows the circuitry of a hearing system, as in FIGS. 1 and 2.

FIG. 5 shows circuitry 500 for use with hearing system 10. Circuitry 500 can be configured to transmit optical power for the output transducer assembly with the optical signal. Circuitry 500 includes an input portion 501 and an output portion 506. Circuitry 500 may use the technique of ratiometric drive, in which two light signals are transmitted, one during "low" signal time, the other during the "high" time of a class A signal.

PWM driver 510 provides a pulse width modulated signal 701, explained more fully below. The pulse width modulated signal from the PWM driver may comprise many known PWM signals, for example at least one of a delta PWM signal, a differential drive PWM signal, a delta-sigma PWM signal or a differential delta-sigma PWM signal.

Logic circuitry can be connected to the output of PWM driver 510. Signal 701 drives light emitter 513 and inverter 519. Inverter 519 produces output signal 512 which drives light emitter 514. Since signal 512 is the inverse of signal 701, light emitter 513 produces light whenever light emitter 514 does not. The light generated by light emitter 513 is conveyed over light channel 520 to light detector 515. The light generated by light emitter 514 is conveyed over light channel 521 to light detector 516. Light detectors 515, 516 are shown connected in series. Light detectors 515, 516 may be photovoltaic cells. Resistors 532, 533 are connected in parallel with detectors 515, 516, respectively, to provide current paths when the output voltage of one detector is lower than the forward diode threshold voltage of the other detector. A power storage device, for example capacitor 547, may also be connected in parallel with detectors 515 and 516 to provide constant voltage power output 545. The power storage device may comprise at least one of a miniature rechargeable battery or a capacitor. Output 545 provides a constant voltage to power active circuit 537, which may comprise an amplifier to drive transducer 538. Light emitter 513 and light emitter 514 are configured to emit light energy so as to power the power storage device and active circuit of output portion 506, such that the output transducer is driven with energy from the light emitter 513 and light emitter 514.

The voltage from the center connection 544 of the two detectors 515, 516 connected in series is connected to drive the input to the active circuit 537. Due to the integrating action of the detectors 515, 516, the voltage from center connection 544 will vary between zero and the maximum voltage in a direct relationship to the ratio of light in channel 520 to the light in channel 521. Optical filters, as described above, can be used. The analog voltage at connection 544 will therefore represent the analog output of PWM converter 510.

Alternatively to connecting the voltage from the active circuit 537 to transducer 538, the active circuit 537 can be coupled to at least two electrodes configured for placement at least partially within the cochlea of the user, such that the user perceives sound in response to electrical stimulation of the cochlea in response to the light output.

Figure 6:
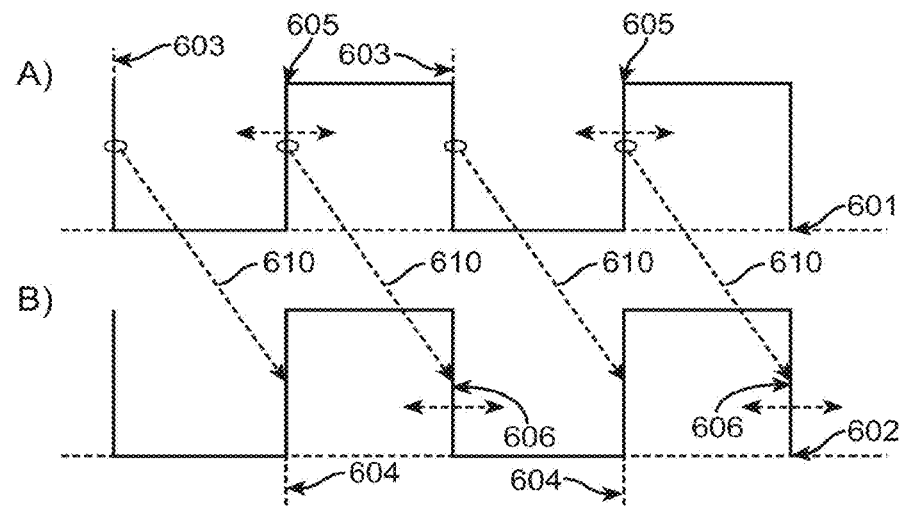
FIG. 6 shows a pulse width modulated signal suitable for use with the transducer assembly.

FIG. 6 a simple pulse-width modulated signal 601 suitable for use with output transducer assembly. Signal 601, which is digital, can take two levels, a high level or a low level, for example 0 V or 5 V. In some embodiments, signal 601 is always low at the start of time window 603 and transitions to the high level at a variable time 605 within window 603. At the end of window 603, signal 601 returns to the low level. The integrated output can be obtained by multiplying the pulse level output by the ratio of time in the high level to the window 603 time.

Analog signals can often take values above and below zero, and the zero output condition of the modulation signal can be defined as the transition at precisely 50 percent of the window time. This type of electrical signal can be referred to a class A signal, wherein the zero (or quiescent) level is represented by a voltage level 50 percent of the maximum voltage.

The digital signal can take zero voltage level as the quiescent state and make excursions away from zero in the positive and negative directions as the input analog signal makes similar excursions. This type of signal can be referred to as class B signal. In an electronic device having limited power and supply voltage, a class B signal can be presented to an output transducer through the technique of differential drive. In the technique of differential drive, two outputs having an inverse relationship with one another are connected to one of the terminals of the output transducer. Connection in this manner effectively doubles the signal voltage supplied to the output transducer.

Driving the output transducer with a simple inverse of one terminal's signal at the opposite terminal will result in a drive signal that integrates to zero during the quiescent point. The drive signal will also contain significant energy at the switching frequency. Although analog filter circuitry may be provided to block the energy at the switching frequency, such circuitry may use components that increase the size of the device.

Instead of filters, the inverted output signal 602 can be shifted by 50 percent of the switching window as indicated by diagonal arrows 610. In the quiescent case, the transition points 603, 605 of signal A will align with transition points 604, 606 of signal B and the levels of the signals will be identical, resulting in zero voltage (A minus B) applied to the terminals of the output transducer.

Alternatively to applying the resulting voltage to the output transducer, the signals can be applied to at least two electrodes configured for placement at least partially within the cochlea of the user, such that the user perceives sound in response to electrical stimulation of the cochlea in response to the light output, as described above.

Figure 7:
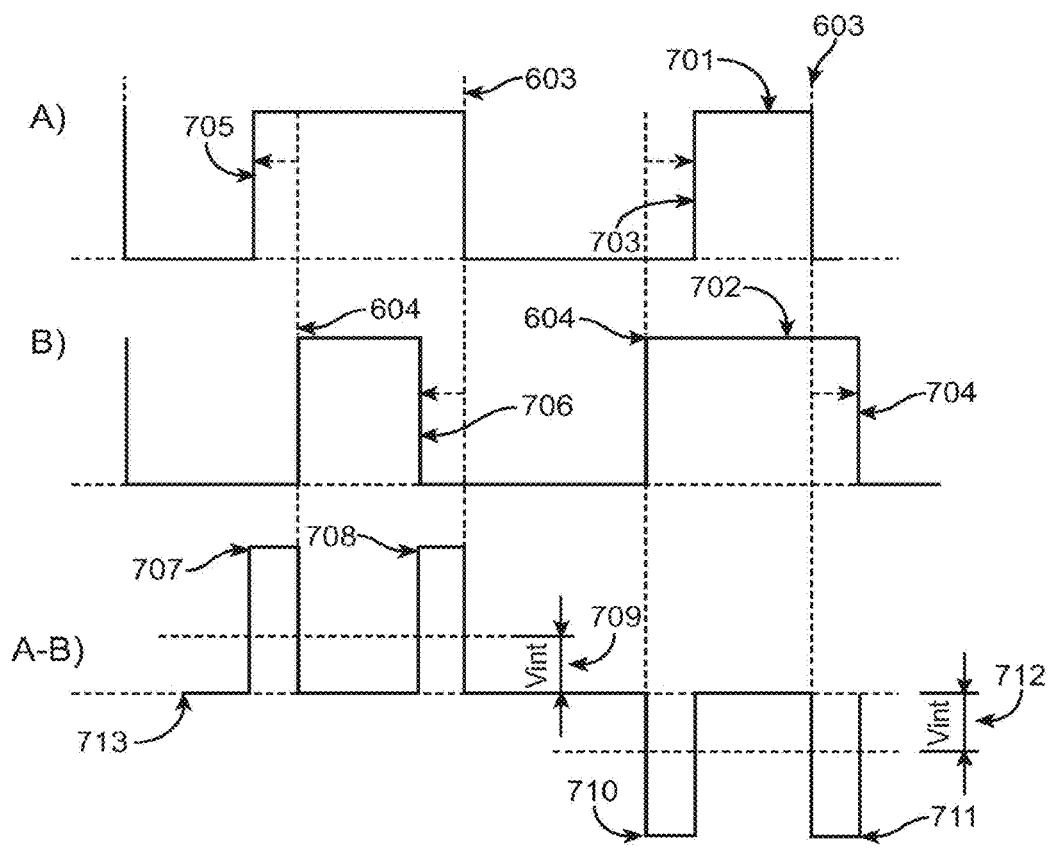
FIG. 7 shows a pair of complementary digital signals, according to embodiments of the present invention.

FIG. 7 shows a pair of complementary class B signals. When the analog output voltage moves above zero, the transition 705 of output signal A 701 moves earlier and occurs before fixed transition 604 of the inverted output signal B 702. The high to low transition 706 of the inverted signal B will occur before the fixed transition 603 of the signal A 701.

The differential output A minus B 713 therefore comprises a positive pulse 707 of width equal to the time difference between times 705 and 604 and a positive pulse 708 of width equal to the time difference between times 706 and 603. When the time differences are equal, the widths of pulses 707 and 708 are equal, and the integrated output voltage Vint 709 is a positive voltage as described above.

When the analog voltage signal is below zero, the transition 703 of output signal A 701 moves later than the fixed transition time 604 of signal B 702, and in a similar fashion transition time 704 of signal B moves later than the fixed transition time 603 of signal A 701. In this case, the differential output A minus B 713 comprises negative pulses 710, 711. The duration of pulse 710 is the time difference between variable time 703 and fixed time 604. The duration of pulse 711 is the time difference between variable time 704 and fixed time 603. The integrated result Vint moves from a positive level 709 defined by the duty cycles of pulses 707 and 708 and a negative level 712 defined by the duty cycle of pulses 710 and 711.

At least some embodiments of the output transducer support electronic circuitry so that the light output signal can be transmitted as pulses defining the transition times of a pulse-width modulated signal, with the transducer signal toggled with each transition event. Depending upon the time response of the transmission and reception path, the duration of the transmitted pulses can be small. Many embodiments include a first high-speed signal transmission path and a second path to transmit power.

Alternatively to coupling the circuitry to an output transducer, the above signals and first high-speed transmission path and second path to transmit power can be coupled to at least two electrodes configured for placement at least partially within the cochlea of the user, such that the user perceives sound in response to electrical stimulation of the cochlea in response to the light output, as described above.

Figure 8:
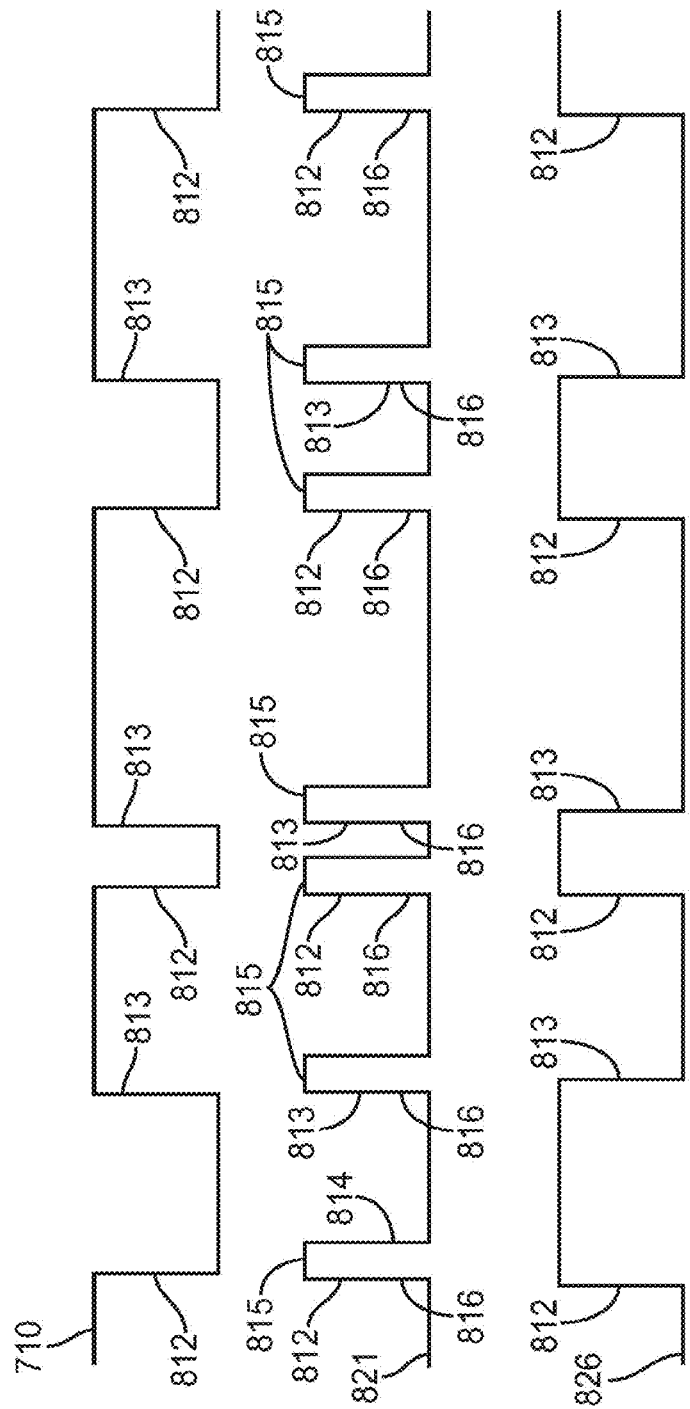
FIG. 8 shows a digital signal, according to embodiments of the present invention.

FIG. 8 shows a PWM signal 701 as previously described, which comprises a single pulse-width modulated signal generated by a PWM driver, as described above. High-to-low transitions 812 occur at fixed times and low-to-high transitions 813 occur at times which vary according to the analog output level. Each transition initiates a constant width pulse 815 from the circuitry that produces signal 821. Trailing edges 814 of the pulses may occur a constant time after their initiation, or at a time which is adjusted to provide intended effects. The signal 821 controls the emission of light from an emitter. At the receiver, the leading edge 816 of the light pulses triggers a toggle circuit which regenerates the signal 701 or an inverse 826 of the signal 701.

Figure 9:
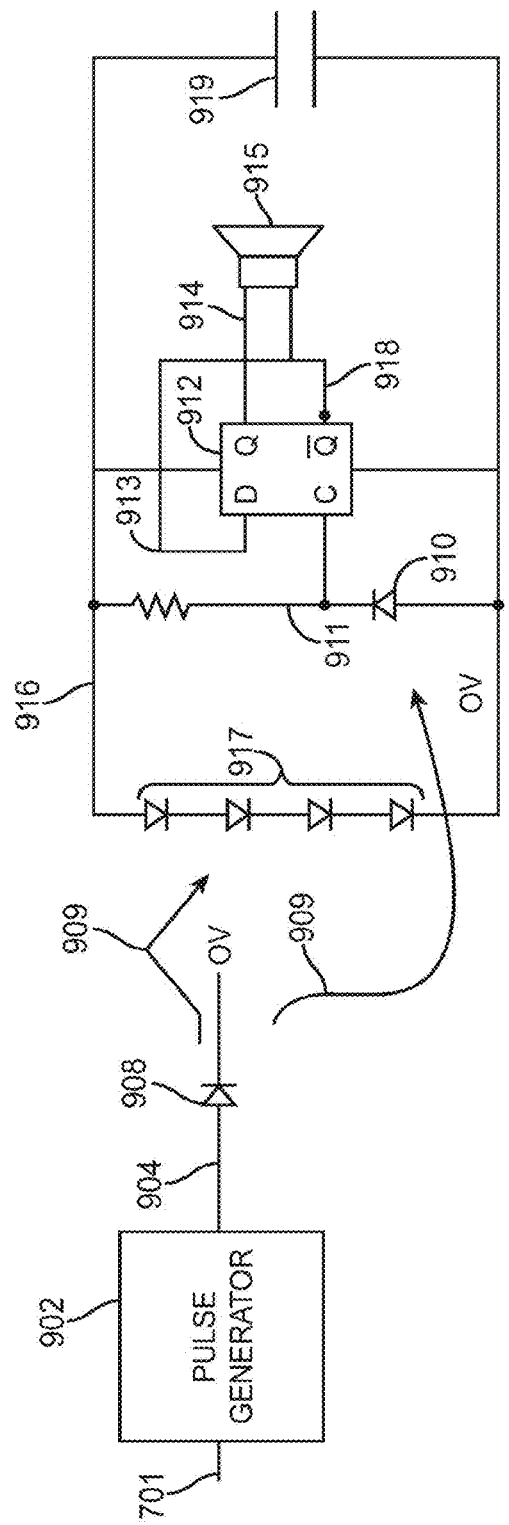
FIG. 9 shows circuitry for use with the signal shown by FIG. 8.

FIG. 9 shows circuitry configured to implement the logic and process the optically transmitted signal, as described above with reference to FIG. 8. PWM signal 701 triggers a pulse generator 902 which is configured to produce a constant-width pulse on its output 904 for each toggle of its input 701, for example constant width pulse 815. Light emitter 908 is driven by the pulse output 904 and the light pulses generated are conducted over light path 909 to high-speed light detector 910 and power generating photovoltaic detector array 917, which may comprise a series array of photovoltaic cells.

The signal 911 generated by light detector 910 is connected to the clock input of D-type flip-flop 912, for example similar to the known 7474 type logic circuits, in which the output 914 is configured to adopt the level of the input 913 upon the rising edge of the clock input 911. A complementary output 918 is configured to adopt the opposite level to the output 914. Such a circuit comprises a toggle when the input 913 is connected to the complementary output 918. The state of output 914, 918 will exchange each time a rising signal edge is presented at clock input 911.

The rising signal edge is presented at clock input 911 by the operation of photodetector 910, shown in FIG. 9 as a reverse-biased photodiode. Power to enable operation of the flip-flop 912 and to provide reverse bias for the photodiode 910 is collected from the light stream by photovoltaic detector array 917 and presented on signal 916 to the circuitry. A power storage device such as a battery or a capacitor 919 can be connected in parallel with photodetector 917 to provide power to flip-flop 912. The power storage device may comprise a miniature rechargeable battery. The voltage presented by photovoltaic detector array 917 may be varied by adjusting the width of pulses generated by pulse generator 902.

Output transducer 915 is connected between the output 914 of the flip-flop 912 and its complementary output 918. An effect of doubling the signal voltage is seen by transducer 915.

Alternatively to coupling the circuitry to transducer 915, the above circuitry can be coupled to at least two electrodes configured for placement at least partially within the cochlea of the user, such that the user perceives sound in response to electrical stimulation of the cochlea in response to the light output, as described above.

Figure 10:
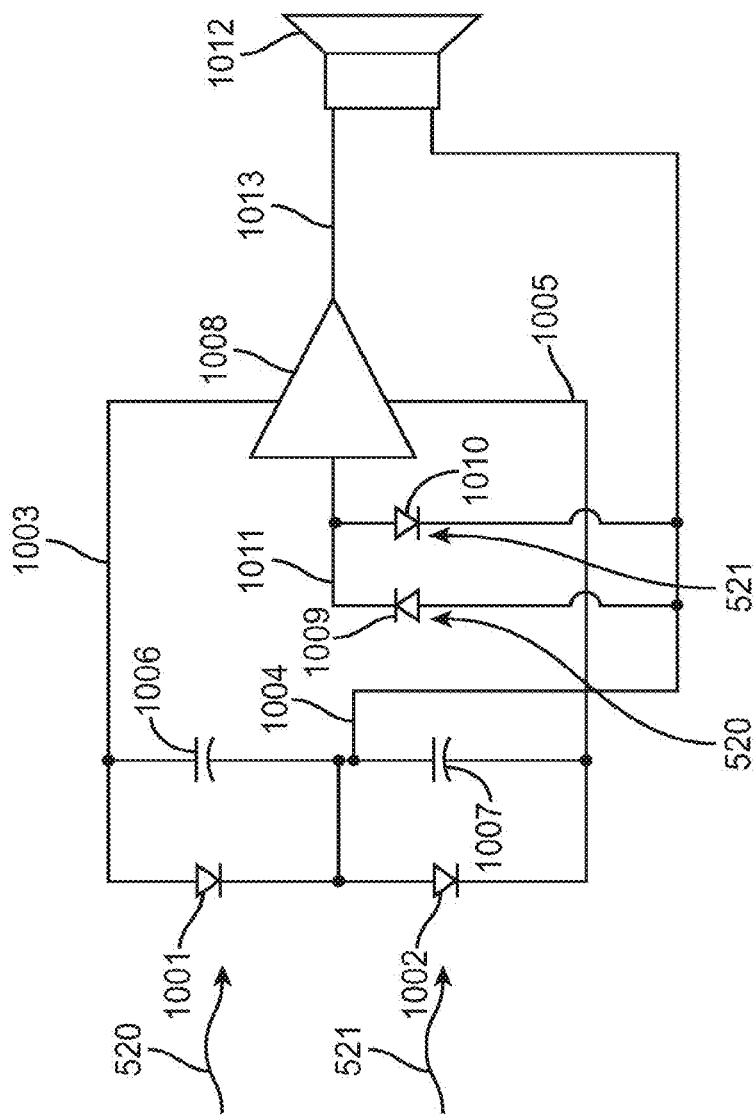
FIG. 10 shows the circuitry of an output transducer assembly for a hearing system, as in FIGS. 1 and 2.

FIG. 10 shows an output transducer assembly configured to operate with two light output channels, for example a first channel 520 and a second channel 521 as described above with reference to FIG. 5. Each light output channel may be exclusive to one of photodetectors 1001 or 1002. Photodetectors 1001 and 1002 are connected in parallel. Due to the integrating characteristics of photodetectors 1001 and 1002, a bipolar analog voltage is produced.

The output light channels can transmit many kinds of light signals, for example signal A 701 and signal B 702 as described above, to generate the bipolar analog voltage. The pulse width modulated signal A and signal B from the PWM driver may comprise many known PWM signals, for example at least one of a delta PWM signal, a differential drive PWM signal, a delta-sigma PWM signal or a differential delta-sigma PWM signal. In some embodiments, light power transmission can be minimized with logic circuitry. For example logic circuitry configured to determine a first condition comprising A and Not B of signal A and signal B and a second condition comprising B and Not A of signal B and signal A. The output from the first condition can drive the first light source and the output from the second condition can drive the second light source, such that energy transmitted with the first and second light source is minimized.

Light from both light channels is made available to power photodetectors 1001 and 1002. Negative terminal 1005 of power photodetector array 1001 is connected as the power return from amplifier 1008. Positive terminal 1003 of the power photodetector array 1001 and 1002 is connected to the positive power supply to amplifier 1008. The center terminal 1004 of the photodetector array is connected as the signal return from the output transducer 1012 and signal photodetectors 1009, 1010 Capacitors 1006 and 1007 are connected in parallel with photodetectors 1001 and 1002, respectively. A power storage device, for example at least one of a miniature rechargeable battery or a capacitor, can be connected across positive terminal 1002 and negative terminal 1005 in parallel with photodetector array 1001 to power amplifier 1008. Capacitors 1006, 1007 may provide the energy storage capability.

Light impinging on the power photodetector array 1001, 1002 generates a positive voltage difference which powers amplifier 1008. Light impinging upon signal photodetector 1009 generates a negative signal at the input 1011 to amplifier 1008, and in a like fashion, light impinging upon photodetector 1010 will generate a positive signal voltage at the input 1011 to amplifier 1008.

Amplifier 1008 produces a signal voltage on output conductor 1013, which is connected to output transducer 1012. Current flows from capacitor 1006 through positive supply conductor 1003, through amplifier 1008 into output transducer 1012 and then flows out on conductor 1004 to the junction of capacitors 1006 and 1007. This current flow charges capacitor 1007 and discharges capacitor 1006.

When the output polarity reverses, current flows from the junction of capacitors 1006 and 1007 through conductor 1004, through output transducer 1012, through amplifier 1008 and return conductor 1005 to capacitor 1007. This current flow charges capacitor 1006 and discharge capacitor 1007. Charge loss can be minimized while driving current though the output transducer 1012.

Power photodetectors 1001 and 1002 act to recharge capacitors 1006 and 1007. Power photodetectors 1001 and 1002 may be series-connected arrays as necessary to provide adequate operating voltage to amplifier 1008, which may incorporate such circuitry as is necessary to accept and amplify bipolar input signals on input 1011. Capacitor 1006 may be replaced and/or combined with a miniature Li-Ion or other rechargeable battery. First power photodetector 1001 and second power photodetector 1002 may each comprise at least one photovoltaic material such as crystalline silicon, amorphous silicon, micromorphous silicon, black silicon, cadmium telluride, copper indium, or gallium selenide. In many embodiments, at least one of first power photodetector 1001 or second power photodetector 1002 comprises black silicon, for example as described in U.S. Pat. Nos. 7,354,792 and 7,390,689 and available under from SiOnyx, Inc. of Beverly, Mass., as described above.

Alternatively coupling the above circuitry to transducer 1012, the above circuitry can be coupled to at least two electrodes configured for placement at least partially within the cochlea of the user, such that the user perceives sound in response to electrical stimulation of the cochlea in response to the light output, as described above.

The above circuits may be configured to bias a photo voltaic such as black silicon so as to optimize the absorption and efficiency of the photovoltaic transducer. For example a biased black silicon photovoltaic can be used for power with a fast photo sensor, such as a reverse biased photodiode, used for signal reception.

Figure 10A:
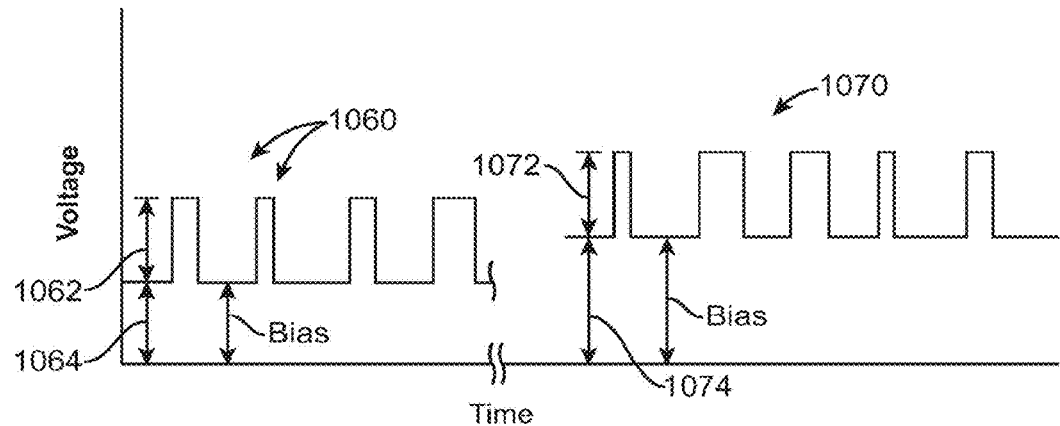
FIG. 10A shows PWM pulses biased in response to energy of the audio signal, according to embodiments of the present invention.

FIG. 10A shows PWM pulses biased in response to energy of the audio signal. First pulses 1060 comprise a low frequency bias, for "DC" bias that changes slowly, for example in response to low pass filtering of the audio signal. The pulses can be combined with the bias, for example with addition, such that an amplitude 1062 of the pulses imposed on the bias remains substantially constant. In response to the energy of the first pulses 1060, the circuitry can adjust the bias, for example increase the bias in response to an increase in energy, for example power, of the audio signal. Second pulses 1070 comprise a second amplitude 1072 that is substantially similar to first amplitude 1062 first pulses 1060. Second bias 1074 is adjusted in response to energy of first pulses 1060, such that second bias 1074 differs substantially from first bias 1064 so as to accommodate the power consumption of the active circuitry and transducer components.

Figure 10B:
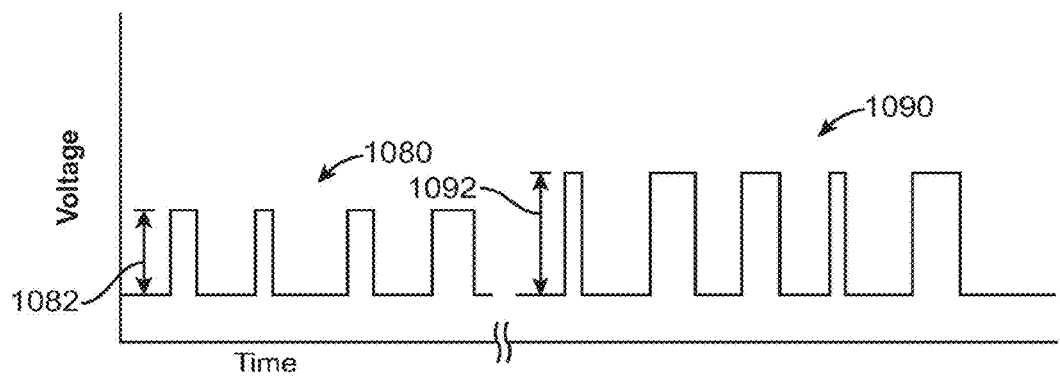
FIG. 10B shows PWM pulses with amplitudes adjusted in response to energy of the audio signal, according to embodiments of the present invention.

FIG. 10B shows PWM pulses with amplitudes adjusted in response to energy of the audio signal. First pulses 1080 comprise a first amplitude 1082 and second pulses 1090 comprise a second amplitude 1092 differs substantially from first amplitude 1082 so as to accommodate the power consumption of the active circuitry and transducer components.

Figure 10C:
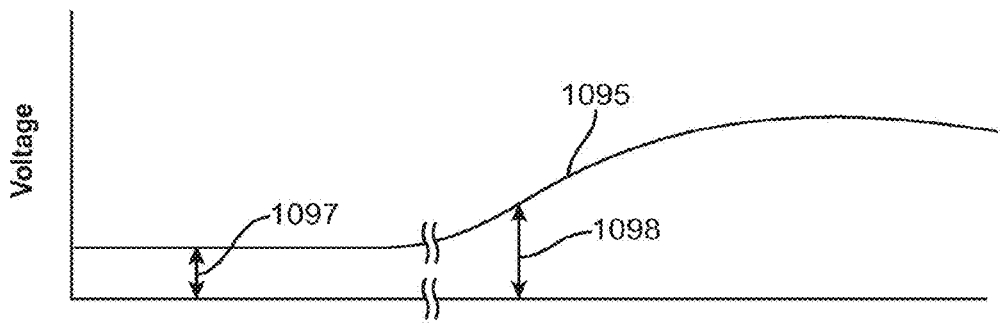
FIG. 10C shows voltage to a second light source configured to transmit power in response to energy of the audio signal, according to embodiments of the present invention.

FIG. 10C shows voltage to a second light source configured to transmit power to the active circuitry components and transducer, so as to accommodate the power consumption of the these components. A first amplitude 1097 is configured to provide sufficient power for first energy of the audio signal, for example first power of the audio signal. A second amplitude 1099 is configured to provide sufficient power for second energy of the audio signal, for example second power of the audio signal.

Figure 11:
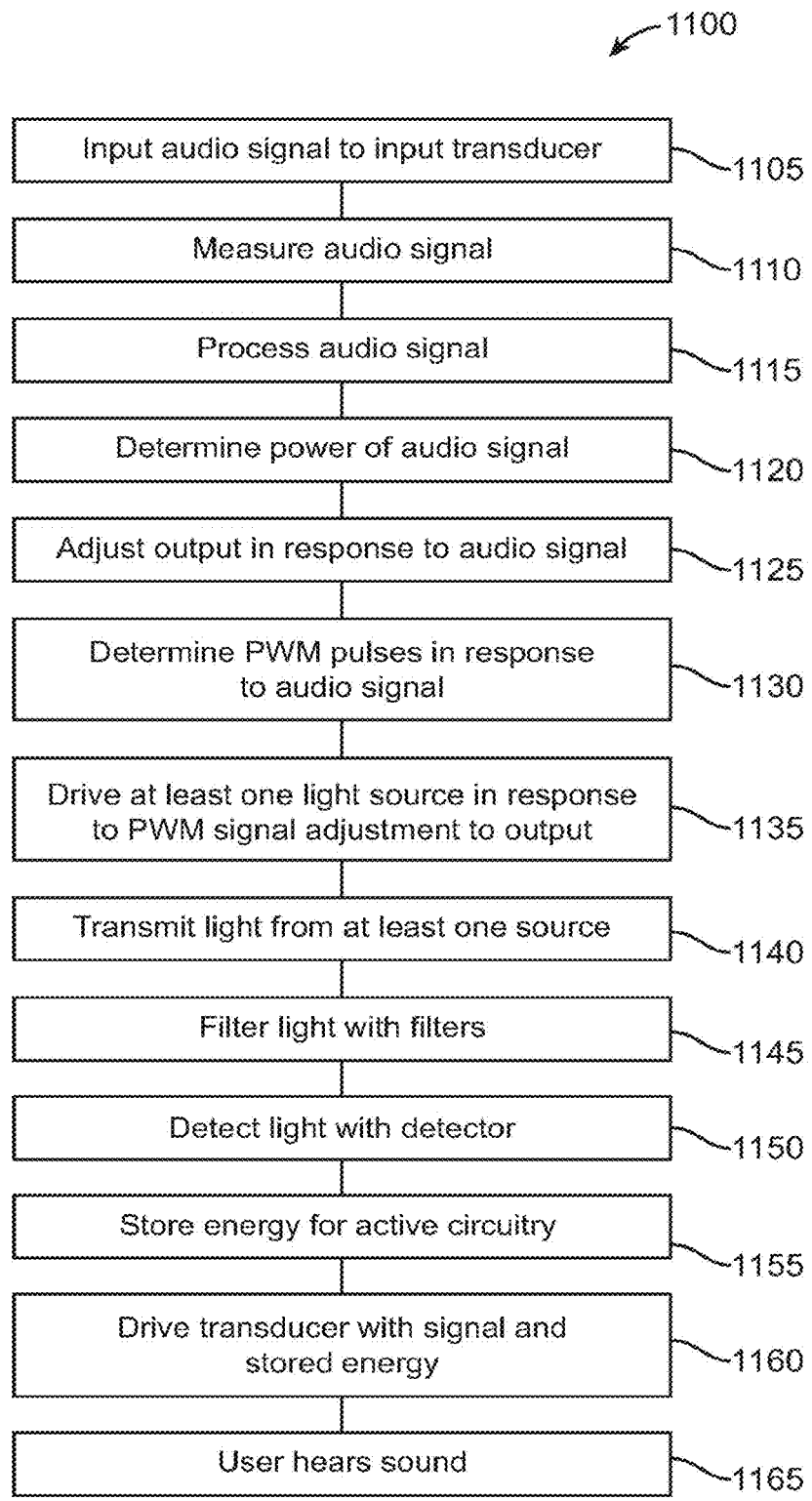
FIG. 11 shows a method of transmitting sound to a user, according to embodiments of the present invention.

FIG. 11 shows a method 1100 of transmitting sound to a user. A step 1105 inputs an audio signal to an input transducer. A step 1110 measures the audio signal. A step 1115 processes the audio signal. The processing can be analog, or digital, or a combination thereof. A step 1120 determines an amount of power of the audio signal. For example with a digital sound processor or with an analog low pass filter, for example. A step 1125 adjusts output in response to the audio signal. The output can be adjusted in many ways, for example with at least one of a DC bias, a sliding scale or an amount of power of a separate channel. A step 1130 determines PWM pulses in response to the audio signal. A step 1135 drives at least one light source in response to the PWM signal and adjustment. A step 1140 transmits the transmits light from the at least one source. A step 1145 filters the transmitted light with filters. A step 1150 detects light with detectors. A step 1155 stores transmitted energy for the active circuitry with a storage device. A step 1160 drives the transducer in response to the PWM signal and the stored energy. With step 1165 a user hears the transmitted audio sound.

Many of the steps of method 1100 can be implemented with the audio processor, described above. For example, the tangible medium of the audio processor may comprise instructions of a computer program embodied therein to implement many of the steps of method 1100.

It should be appreciated that the specific steps illustrated in FIG. 11 provides a particular method transmitting an audio signal, according to some embodiments of the present invention. Other sequences of steps may also be performed according to alternative embodiments. For example, alternative embodiments of the present invention may perform the steps outlined above in a different order. Moreover, the individual steps illustrated in FIG. 8 may include multiple sub-steps that may be performed in various sequences as appropriate to the individual step. Furthermore, additional steps may be added or removed depending on the particular applications. One of ordinary skill in the art would recognize many variations, modifications, and alternatives.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A device to transmit an audio signal, the device comprising:
    at least one light source configured to transmit the audio signal using an optical signal;
    at least one optical detector configured to detect the audio signal and generate at least one electrical signal in response to the detected audio signal;
    an output transducer assembly supported with and configured to vibrate an eardrum wherein the output transducer assembly is driven in response to the at least one electrical signal;
    circuitry configured to receive the audio signal and to transmit the audio signal with a pulse modulated signal, wherein power for the output transducer assembly is transmitted with the optical signal;
    wherein the circuitry is further configured to determine a first energy of the audio signal and a second energy of the audio signal, the circuitry configured to provide a first bias to the pulse modulated signal in response to the first energy of the audio signal and to provide a second bias to the pulse modulated signal in response to the second energy of the audio signal, the first bias different from the second bias in order to accommodate substantially different power consumption of the output transducer assembly in response to the first energy different from the second energy.

2. The device of claim 1, wherein the at least one optical detector comprises at least one of crystalline silicon, amorphous silicon, micromorphous silicon, black silicon, cadmium telluride, copper indium, gallium selenide, or indium gallium arsenide.

3. The device of claim 1, wherein the output transducer assembly comprises at least one of a piezo electric transducer, a flex tensional transducer, a wire coil, a magnet, or an acoustic speaker.

4. The device of claim 1, wherein the circuitry is configured to receive the audio signal from an input transducer, and wherein the pulse modulated signal is a pulse width modulated signal.

5. The device of claim 4, wherein the pulse width modulated signal comprises at least one of a delta PWM signal, a differential drive PWM signal, a delta-sigma PWM signal, or a differential delta-sigma PWM signal.

6. The device of claim 1, wherein the circuitry is coupled to an input configured to receive the audio signal, the circuitry is coupled to the at least one light source, and the circuitry is configured to adjust an output of the at least one light source to power the output transducer assembly in response to the audio signal.

7. The device of claim 6, wherein the circuitry is configured measure the audio signal to determine one or more of the first energy or the second energy of the audio signal and to adjust an amount of energy transmitted with the at least one light source in response to the determined one or more of the first energy or the second energy of the audio signal.

8. The device of claim 6, wherein the circuitry is configured to adjust at least one of a DC bias or an amplitude of pulses of the at least one light source in response to the audio signal to power the circuitry.

9. The device of claim 6, wherein the at least one light source comprises a first light source configured to transmit the audio signal and a second light source configured to transmit the power for the output transducer assembly, and wherein the circuitry is configured to adjust an amount of power transmitted with the second light source in response to the audio signal.

10. The device of claim 6, wherein the circuitry comprises a sound processor configured to measure the audio signal and to adjust the output of the at least one light source to power the circuitry in response to the audio signal.

11. The device of claim 1, wherein the audio signal is transmitted with at least one wavelength of light comprising at least one of an ultraviolet light, a visible light, or an infrared light.

12. The device of claim 1, wherein the first or second bias is increased in response to an increase in the first or second energy of the audio signal.

13. The device of claim 1, wherein the at least one optical detector converts light energy into electrical energy and the output transducer assembly converts the electrical energy into mechanical energy.

14. The device of claim 13, wherein the mechanical energy is vibration.

15. A method of transmitting an audio signal having a first energy and a second energy different from the first energy, the method comprising:
    receiving the audio signal with circuitry coupled to an input and at least one light source, wherein the circuitry determines the first energy of the audio signal and the second energy of the audio signal;
    emitting at least one pulse modulated wavelength of light from the at least one light source using an optical signal and wherein the circuitry outputs a first amount of bias and a second amount of bias from the at least one light source;
    detecting the at least one wavelength of light with at least one detector to generate an electrical signal; and
    vibrating an eardrum with a transducer, the transducer being a part of an output transducer assembly, in response to the electrical signal, wherein the first amount of bias differs from the second amount of bias in order to accommodate substantially different power consumption of the transducer in response to the first energy different from the second energy and wherein power for the output transducer assembly is transmitted with the optical signal.

16. The method of claim 15, wherein the transducer is supported by the eardrum.

17. A method of stimulating a target tissue with an audio signal having a first energy and a second energy different from the first energy, the method comprising:
    receiving the audio signal with circuitry coupled to an input and at least one light source, wherein the circuitry determines the first energy of the audio signal and the second energy of the audio signal;
    emitting a pulse modulated light signal using an optical signal from the at least one light source and wherein the circuitry outputs a first amount of bias from the at least one light source and a second amount of bias from the at least one light source to power active circuitry;
    detecting the pulse modulated light signal to generate an electrical signal in response to the pulse modulated light signal; and
    stimulating the target tissue with a transducer in response to the electrical signal wherein the transducer is a part of an output transducer assembly;
    wherein the first amount of bias differs from the second amount of bias in order to accommodate substantially different power consumption of the transducer in response to the first energy different from the second energy and wherein the output transducer assembly is transmitted with the optical signal.

18. The method of claim 17 wherein the target tissue is stimulated with a vibration.

* * * * *